(12) United States Patent
Dobrinsky et al.

(10) Patent No.: US 10,894,103 B2
(45) Date of Patent: Jan. 19, 2021

(54) ULTRAVIOLET-BASED BATHROOM SURFACE SANITIZATION

(71) Applicant: Sensor Electronic Technology, Inc., Columbia, SC (US)

(72) Inventors: Alexander Dobrinsky, Silver Springs, MD (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 14 days.

(21) Appl. No.: 16/460,006

(22) Filed: Jul. 2, 2019

(65) Prior Publication Data

US 2019/0336629 A1 Nov. 7, 2019

Related U.S. Application Data

(63) Continuation-in-part of application No. 15/700,621, filed on Sep. 11, 2017, now Pat. No. 10,369,239, which is a continuation-in-part of application No. 14/934,464, filed on Nov. 6, 2015, now Pat. No. 9,757,486.

(60) Provisional application No. 62/076,244, filed on Nov. 6, 2014.

(51) Int. Cl.
*A61L 2/10* (2006.01)
*E03D 9/00* (2006.01)

(52) U.S. Cl.
CPC ............... *A61L 2/10* (2013.01); *E03D 9/002* (2013.01); *A61L 2202/11* (2013.01); *A61L 2202/14* (2013.01)

(58) Field of Classification Search
CPC .................................. A61L 2/10; E03D 9/002
USPC ............................................................. 4/233
See application file for complete search history.

(56) References Cited

U.S. PATENT DOCUMENTS

| | | |
|---|---|---|
| 3,829,906 A | 8/1974 | McPhee |
| 3,919,726 A | 11/1975 | Godwin et al. |
| 4,091,473 A | 5/1978 | Matthews et al. |
| 4,210,973 A | 7/1980 | Decaux |
| 4,301,558 A | 11/1981 | Decaux |
| 4,726,079 A | 2/1988 | Signori et al. |
| 4,797,959 A | 1/1989 | Decaux |
| 4,853,982 A | 8/1989 | Martinval |
| 5,090,069 A | 2/1992 | Decaux |
| 5,263,209 A | 11/1993 | Pattee |
| 5,279,008 A | 1/1994 | Ritter |
| 5,446,928 A | 9/1995 | Daniels |
| 5,642,531 A | 7/1997 | Holtom et al. |
| 5,647,074 A | 7/1997 | White, Jr. et al. |

(Continued)

OTHER PUBLICATIONS

Baker, L., U.S. Appl. No. 15/700,621, Notice of Allowance, dated Mar. 21, 2019, 8 pages.

(Continued)

*Primary Examiner* — Christine J Skubinna
(74) *Attorney, Agent, or Firm* — LaBatt, LLC

(57) ABSTRACT

A solution for cleaning and/or sterilizing one or more surfaces in a bathroom is provided. The sterilization can be performed using ultraviolet sources, which can emit ultraviolet radiation directed onto the surface(s). The cleaning can be performed using a fluid, such as water, that is flowed over the surface(s). The surface(s) can include at least a seat of a toilet and/or other surfaces associated with the toilet.

20 Claims, 12 Drawing Sheets

(56) References Cited

U.S. PATENT DOCUMENTS

| | | |
|---|---|---|
| 5,664,867 A | 9/1997 | Martin et al. |
| 5,765,237 A | 6/1998 | Okamoto et al. |
| 5,806,105 A | 9/1998 | Yu |
| 5,963,991 A | 10/1999 | Agosti et al. |
| 6,076,197 A | 6/2000 | Yeung |
| 7,553,456 B2 | 6/2009 | Gaska et al. |
| 7,634,996 B2 | 12/2009 | Gaska et al. |
| 8,060,953 B1 | 11/2011 | Dorra |
| 8,277,734 B2 | 10/2012 | Koudymov et al. |
| 8,769,729 B2 | 7/2014 | Nishimura et al. |
| 8,980,178 B2 | 3/2015 | Gaska et al. |
| 9,006,680 B2 | 4/2015 | Bettles et al. |
| 9,138,499 B2 | 9/2015 | Bettles et al. |
| 9,380,918 B2 | 7/2016 | Murphy et al. |
| 9,757,486 B2 | 9/2017 | Dobrinsky et al. |
| 9,828,755 B1 | 11/2017 | Clements |
| 10,369,239 B2 | 8/2019 | Dobrinsky et al. |
| 2004/0045082 A1 | 3/2004 | Marras |
| 2006/0097189 A1 | 5/2006 | Lim |
| 2006/0206997 A1 | 9/2006 | Chiang et al. |
| 2008/0134420 A1 | 6/2008 | Ho |
| 2010/0296971 A1* | 11/2010 | Gaska ............... A61L 2/10 422/62 |
| 2013/0048545 A1 | 2/2013 | Shatalov et al. |
| 2013/0270445 A1 | 10/2013 | Gaska et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0137318 A1 | 5/2014 | Dorra |
| 2014/0202962 A1 | 7/2014 | Bilenko et al. |
| 2015/0008167 A1 | 1/2015 | Shturm et al. |
| 2015/0069270 A1 | 3/2015 | Shur et al. |
| 2015/0165079 A1 | 6/2015 | Shur et al. |
| 2015/0217011 A1 | 8/2015 | Bettles et al. |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0058020 A1 | 3/2016 | Shur et al. |
| 2016/0074547 A1 | 3/2016 | Dobrinsky et al. |
| 2016/0077278 A1 | 3/2016 | Dobrinsky et al. |
| 2016/0077292 A1 | 3/2016 | Dobrinsky et al. |
| 2016/0088868 A1 | 3/2016 | Dobrinsky et al. |
| 2016/0106873 A1 | 4/2016 | Dobrinsky et al. |
| 2016/0114067 A1 | 4/2016 | Dobrinsky et al. |
| 2016/0114186 A1 | 4/2016 | Dobrinsky et al. |
| 2018/0021465 A1 | 1/2018 | Dobrinsky et al. |

OTHER PUBLICATIONS

Baker, L., U.S. Appl. No. 15/700,621, Office Action 2, dated Oct. 5, 2018, 4 pages.

Baker, L., U.S. Appl. No. 15/700,621, Office Action1, dated Apr. 3, 2018, 26 pages.

Baker, L., U.S. Appl. No. 14/934,464, Notice of Allowance, dated May 10, 2017, 7 pages.

Baker, L., U.S. Appl. No. 14/934,464, Office Action1, dated Nov. 10, 2016, 22 pages.

Hwang, C., International Application No. PCT/US2015/059420, International Search Report and Written Opinion, dated Feb. 17, 2016, 15 pages.

* cited by examiner

ULTRAVIOLET-BASED BATHROOM SURFACE SANITIZATION

REFERENCE TO RELATED APPLICATIONS

The current application is a continuation-in-part of U.S. patent application Ser. No. 15/700,621, filed on 11 Sep. 2017, which is a continuation-in-part of U.S. patent application Ser. No. 14/934,464, filed on 6 Nov. 2015, and issued as U.S. Pat. No. 9,757,486, which claims the benefit of U.S. Provisional Application No. 62/076,244, filed on 6 Nov. 2014, each of which is hereby incorporated by reference.

TECHNICAL FIELD

The disclosure relates generally to surface sterilization, and more particularly, to sterilization of a surface, such as one or more components of a toilet, using ultraviolet light.

BACKGROUND ART

The bathroom (e.g., water closet or lavatory) is the single, most polluted room in any home or public building. The continual use of bleaches, detergents and antibiotics to clean the bathroom are harmful to the environment and produce resistant strains, which become progressively more difficult to control. The use of chemicals is short lived and is generally used after such pollution has become established. Nevertheless, there is a general concern with both the public and health authorities that cleanliness around lavatories needs continuous attention.

There have been a number of approaches describing toilets with a self-cleaning bowl. Cleaning a toilet is important for both aesthetic and health reasons. In addition to the waste that may soil the toilet bowl, a great many water supply systems provide water having bacteria, minerals, or other matter that cause stains and deposits when the water is left stagnant for any period of time, particularly around the water line of a toilet. Cleaning toilets is not a pleasant task and few people are likely to enjoy the job. As a result, a toilet may not be cleaned for a long period of time. The longer the time between cleanings, the more difficult the task becomes, e.g., because the stains set into the porcelain and require major scrubbing and chemicals to remove them.

In an illustrative approach, a sanitary unit comprising at least one vessel, such as a bowl, basin, or a lavatory pan, which is movable between a position of use and a cleaning position. The unit comprises a rotary brush for cleaning the vessel when the latter is in its cleaning position and means for controlling the displacement of the vessel between the two positions and means for actuating the rotary brush.

Another approach provides a sanitary cell with an automatic cleaning device for the toilet bowl. The sanitary cell includes a sanitary chamber, a first technical equipment chamber for accommodating toilet bowl cleaning appliances, and a wall, which separates the two chambers and which supports, on its opposite sides, two toilet bowls which are located in the sanitary and first technical equipment chambers, respectively. The toilet bowl located in the sanitary chamber has an opening, which points upwardly. The toilet bowl located in the first technical equipment chamber has an opening, which points downwardly. A second technical equipment chamber is located beneath the floor of the sanitary chamber. A separating wall pivots about a horizontal axis to enable the pivoting of the toilet bowls from the first technical equipment chamber, through the second technical equipment chamber, and into the sanitary chamber, so that the toilet bowls can be cleaned. The sanitary and technical equipment chambers have respective openings in the area of the respective bowls so as to accommodate their pivotal movement.

Still another approach describes a self-cleaning water closet wherein either the bowl or a specifically provided cabinet-type enclosure is pivotally movable between a first non-cleaning position and a second cleaning position. When in the cleaning position, the cabinet-type enclosure sealably encloses at least a portion of the bowl before washing begins.

A hospital patient care unit has been described, which consists of a folding toilet in a compact cabinet wherein the cowl of the toilet is removable so that the unit can be used either as a bedpan or in the normal manner. The unit is designed so that when it is closed, the bowl is automatically flushed and washed out and an interlock prevents opening the cabinet while the flushing operation is taking place.

A height adjustable toilet bowl has been described, which includes a water-actuated cylinder for moving it between a low position and a high position. The toilet bowl has a cleaning water circuit adapted to be connected to a water supply pipe, a hose interposed between the cleaning water circuit and the water supply pipe and an outlet pipe connected to a discharge duct through an extensible pipe. The water-actuated cylinder is a flexible cylinder connectable selectively to the water supply pipe and to the cleaning water circuit through a three position valve, a pipe being interposed between the flexible cylinder and the three position valve.

A previous approach provides a public toilet facility which is self-cleaning, automatic, and handicapped accessible. The facility offers a toilet that not only lowers from a vertical position to a horizontal position, but can also be adjusted vertically to different heights. High-pressure water jet nozzles are provided within the facility for high pressure cleaning of the toilet bowl and seat when the bowl is in the vertical position. The compact facility has a semicircular door, which is stored behind the equipment and machinery compartment when the facility is unoccupied.

Still another self-cleaning sanitation module has been described, which comprises a toilet pan movable between a use position and a cleaning position in which it is behind a separating wall. A back is provided which is movable between two positions, a use position and a cleaning position in which the back is disposed vertically above the pan. The displacement of the pan and the back between their use position and their cleaning position is performed in such a way that there is always a very small gap between the back and the pan.

Another approach describes a flush pot assembly having a pot, which is concealed when it is not being used. The pot can be easily accessed for use and washed with washing water after use even by a disabled person or a hospital patient. The flush pot assembly includes a pot connected to a flexible drain hose for passing washing water. The pot is provided such that it is integral with a back surface of a door. The door can be opened and closed and constitutes part of one side of a room. The flexible drain hose is connected between the pot and a drainpipe, which leads to the outside of the room. The pot is moved into the room by opening the door and is accommodated in a space outside the room by closing the door.

A sanitary unit having an automatic cleansing cycle has been described, which comprises a lockable enclosure in which a partition defines a usage zone and a maintenance zone. A bowl is mounted for rotation between a utilization position in which it projects horizontally from the partition in said usage zone and a cleaning position in which it is tipped up into an opening in the partition so as to empty it into the maintenance zone. The upwards opening of the bowl is separated into two sections by a partition wall which extends upwardly to cooperate with the front walls of the bowl to form a rim surrounding the utilization section of the bowl. The bottom of the partition wall stops short of the base of the bowl to define an orifice and the rear section of the bowl forms an evacuation passage from the evacuation orifice rearwards to the maintenance zone when the bowl is tipped up.

In another approach, a sanitary unit of the type comprising a vessel, which is mounted to be movable between a position of use and a cleaning position is described. In the swung over cleaning position, the pan faces the rotary brush and the back part closes the upper part of the drum of the brush so as to preclude any projection of water outside the drum. Further, the drum comprises a water supply system provided with radial perforations, which extend throughout the generatrix of the brush so as to spray the latter and complete the cleaning. The fluid supplied by the system may be pure water or water to which an anti-bacteria or anti-microbe disinfecting solution has been added.

A lift to flush toilet stool has been described, which includes a bowl supported above the ground, a flexible hose connecting the bowl to a sewer pipe and a support member for releasably retaining the flexible hose in a trap configuration. The bowl is lifted and the flexible hose substantially straightened to flush the toilet stool.

An approach describes an adjustable toilet mounted on the wall of a bathroom. The toilet is raised and lowered by an electrically driven motor. By raising and lowering the toilet, the elderly, the handicapped, and children are aided in the use of the toilet. The toilet provides electrical limit switches for stopping the motor at a desired height above the bathroom floor.

Another approach discusses an automatic toilet seat cleaning system including a movable toilet seat supported on a toilet bowl of a toilet in front of a toilet water tank and moved between a front side position and a rear side position, a fixed first motor, a transmission mechanism controlled by the first motor to turn the toilet seat horizontally when the toilet seat is moved to the rear side position, a fixed second motor, a wheel brush turned by the second motor to clean the toilet seat when the toilet seat is moved to the rear side position and turned by the transmission mechanism, a waste water tank adapted to hold waste water falling from the movable toilet seat, a water tube adapted to guide clean water to the wheel brush for cleaning the toilet seat, and an electrical dryer controlled to dry the toilet seat.

In still another approach, a toilet, particularly for public use, comprising a toilet bowl, the upper side of which is provided with a toilet seat, and a cleaning device by means of which at least the toilet seat can be cleaned is described. Said toilet seat is movable between an operating position and a cleaning position. The inner cleaning device comprises a housing which forms an inner cleaning chamber and is provided with cleaning elements that are placed therein. The toilet seat partly extends into the housing and is rotatable around a vertical axis in the cleaning position.

SUMMARY OF THE INVENTION

The inventors note that none of the known prior art approaches utilize ultraviolet radiation for cleaning surfaces in a bathroom. Furthermore, none of these approaches utilizes feedback control based on a fluorescence analysis of the surface and/or reflective properties of the surface in order to complete a cleaning process and/or verify an absence of microorganisms. Still further, the prior art approaches fail to address slow changes in a microorganism population on the surface, such as the toilet seat, during its vacancy state.

Aspects of the invention provide a solution for cleaning and/or sterilizing one or more surfaces in a bathroom. The sterilization can be performed using ultraviolet sources, which can emit ultraviolet radiation directed onto the surface (s). The cleaning can be performed using a fluid, such as water, that is flowed over the surface(s). The surface(s) can include at least a seat of a toilet and/or other surfaces associated with the toilet.

A first aspect of the invention provides a system comprising: a toilet including a seat; a fluorescent ultraviolet source configured to emit ultraviolet radiation directed at the seat to excite a fluorescent signal from a target contaminant; a fluorescent sensor for detecting the fluorescent signal and evaluating a presence of the target contaminant; and a sterilizing ultraviolet source configured to emit ultraviolet radiation directed at the seat to sterilize the seat.

A second aspect of the invention provides a system comprising: a toilet, wherein the toilet includes a fluid source for cleaning a seat of the toilet with a fluid; and a set of ultraviolet sources configured to generate ultraviolet radiation directed onto a set of surfaces associated with the toilet, wherein the set of surfaces includes at least the seat of the toilet.

A third aspect of the invention provides a bathroom including: a set of fixtures, wherein at least one of the set of fixtures includes: a fluorescent ultraviolet source configured to emit ultraviolet radiation directed at a surface of the fixture to excite a fluorescent signal from a target contaminant; a fluorescent sensor for detecting the fluorescent signal and evaluating a presence of the target contaminant; and a sterilizing ultraviolet source configured to emit ultraviolet radiation directed at the surface to sterilize the surface.

A fourth aspect of the invention provides a system comprising: a toilet including a seat; a visible light source configured to emit visible light directed at the seat; a visible light sensor for detecting visible light reflected from the seat; a sterilizing ultraviolet source configured to emit ultraviolet radiation directed at the seat; and a computer system for correlating the reflected visible light with a presence of contamination on the seat and for operating the sterilizing ultraviolet source to sterilize the seat in response to the evaluating indicating the presence of contamination on the seat.

A fifth aspect of the invention provides a system comprising: a toilet, wherein the toilet includes: a cleaning chamber; means for moving the seat into the cleaning chamber; and a set of fluid sources for cleaning the seat using a fluid within the cleaning chamber; and a sterilizing ultraviolet source configured to generate ultraviolet radiation directed onto the seat, wherein the sterilizing ultraviolet source is located within the cleaning chamber.

A sixth aspect of the invention provides a bathroom including: a set of fixtures; a visible light source configured to emit visible light directed at a surface of at least one of the set of fixtures; a visible light sensor for detecting visible light reflected from the surface of the at least one of the set of fixtures; a sterilizing ultraviolet source configured to emit ultraviolet radiation directed at the surface of the at least one of the set of fixtures; and a computer system for correlating the reflected visible light with a presence of contamination on the surface and for operating the sterilizing ultraviolet source to sterilize the surface in response to the evaluating indicating the presence of contamination on the surface.

A seventh aspect of the invention provides a system comprising: means for detecting radiation from a seat of a toilet; a first ultraviolet source configured to emit ultraviolet radiation at a first wavelength directed at the seat; second ultraviolet source configured to emit ultraviolet radiation at a second wavelength directed at the seat; and a computer system for correlating the detected radiation with a presence of contamination on the seat and for operating at least one of: the first ultraviolet source or the second ultraviolet source, to sterilize the seat in response to the evaluating indicating the presence of contamination on the seat.

An eighth aspect of the invention provides a system comprising: a toilet including a seat; means for detecting radiation from the seat of the toilet; a first ultraviolet source configured to emit ultraviolet radiation at a first wavelength directed at the seat; second ultraviolet source configured to emit ultraviolet radiation at a second wavelength directed at the seat, wherein at least one of: the first ultraviolet source or the second ultraviolet source, is isolated from an area for the seat by an ultraviolet transparent material; and a computer system for correlating the detected radiation with a presence of contamination on the seat and for operating at least one of: the first ultraviolet source or the second ultraviolet source, to sterilize the seat in response to the evaluating indicating the presence of contamination on the seat.

A ninth aspect of the invention provides a bathroom including: a set of fixtures; means for detecting radiation from a surface of at least one of the set of fixtures; a first ultraviolet source configured to emit ultraviolet radiation at a first wavelength directed at the surface of the at least one of the set of fixtures; second ultraviolet source configured to emit ultraviolet radiation at a second wavelength directed at the surface of the at least one of the set of fixtures; and a computer system for correlating the detected radiation with a presence of contamination on the surface of the at least one of the set of fixtures and for operating at least one of: the first ultraviolet source or the second ultraviolet source, to sterilize the surface of the at least one of the set of fixtures in response to the evaluating indicating the presence of contamination on the surface of the at least one of the set of fixtures.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 7A and 7B show alternate configurations of another illustrative toilet including a cleaning chamber according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
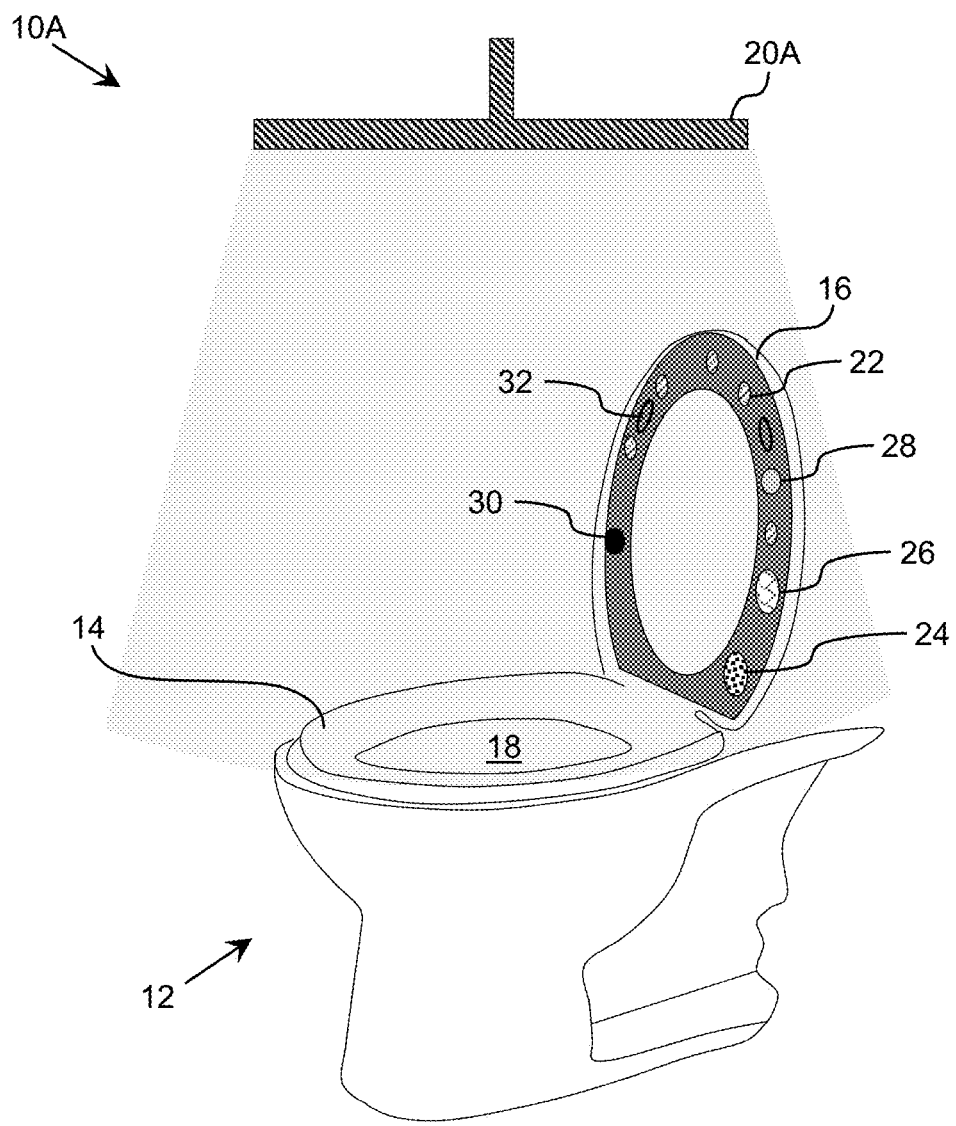
FIGS. 1A and 1B show illustrative environments for cleaning one or more surfaces of a toilet using ultraviolet radiation according to embodiments.

As indicated above, aspects of the invention provide a solution for cleaning and/or sterilizing one or more surfaces in a bathroom. The sterilization can be performed using ultraviolet sources, which can emit ultraviolet radiation directed onto the surface(s). The cleaning can be performed using a fluid, such as water, that is flowed over the surface (s). The surface(s) can include at least a seat of a toilet and/or other surfaces associated with the toilet.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As used herein, blue-ultraviolet (blue-UV) radiation has a wavelength between approximately 380 nm to 420 nm.

As also used herein, a material/structure is "transparent" when the material/structure allows at least ten percent of radiation having a target wavelength, which is radiated at a normal incidence to an interface of the layer, to pass there through. Furthermore, as used herein, a material/structure is "reflective" when the material/structure has a reflection coefficient of at least thirty percent for radiation having a target wavelength. In a more particular embodiment, a material/structure is "highly reflective" when the material/structure has a reflection coefficient of at least eighty percent for radiation having a target wavelength. In an embodiment, the target wavelength of the radiation corresponds to a wavelength of radiation emitted or sensed (e.g., peak wavelength+/–five nanometers) by an active region of an optoelectronic device during operation of the device. For a given layer, the wavelength can be measured in a material of consideration and can depend on a refractive index of the material.

Aspects of the invention provide a solution in which surface(s) are sterilized using ultraviolet radiation. To this extent, the ultraviolet radiation can be directed at the surface(s) in such a manner as to harm (e.g., suppress growth of, reduce an amount of, kill, damage, injure, etc.) any organisms that may be present on the surface(s). The organism(s) can comprise any combination of various types of organisms, such as bacteria, viruses, protozoa, biofilms, mold, and/or the like. The discussion herein refers to the sterilization of one or more surfaces. As used herein, "sterilizing" and "sterilization" refer to harming one or more target organisms, and include purification, disinfection, sanitization, and/or the like. Furthermore, as used herein a "sterilized surface" includes a surface that is devoid of any live organisms, a surface that is devoid of any live targeted organisms (but which may include non-targeted organisms), and a surface that includes some live targeted organism(s), but which is substantially free of such organism(s).

Figure 1B:
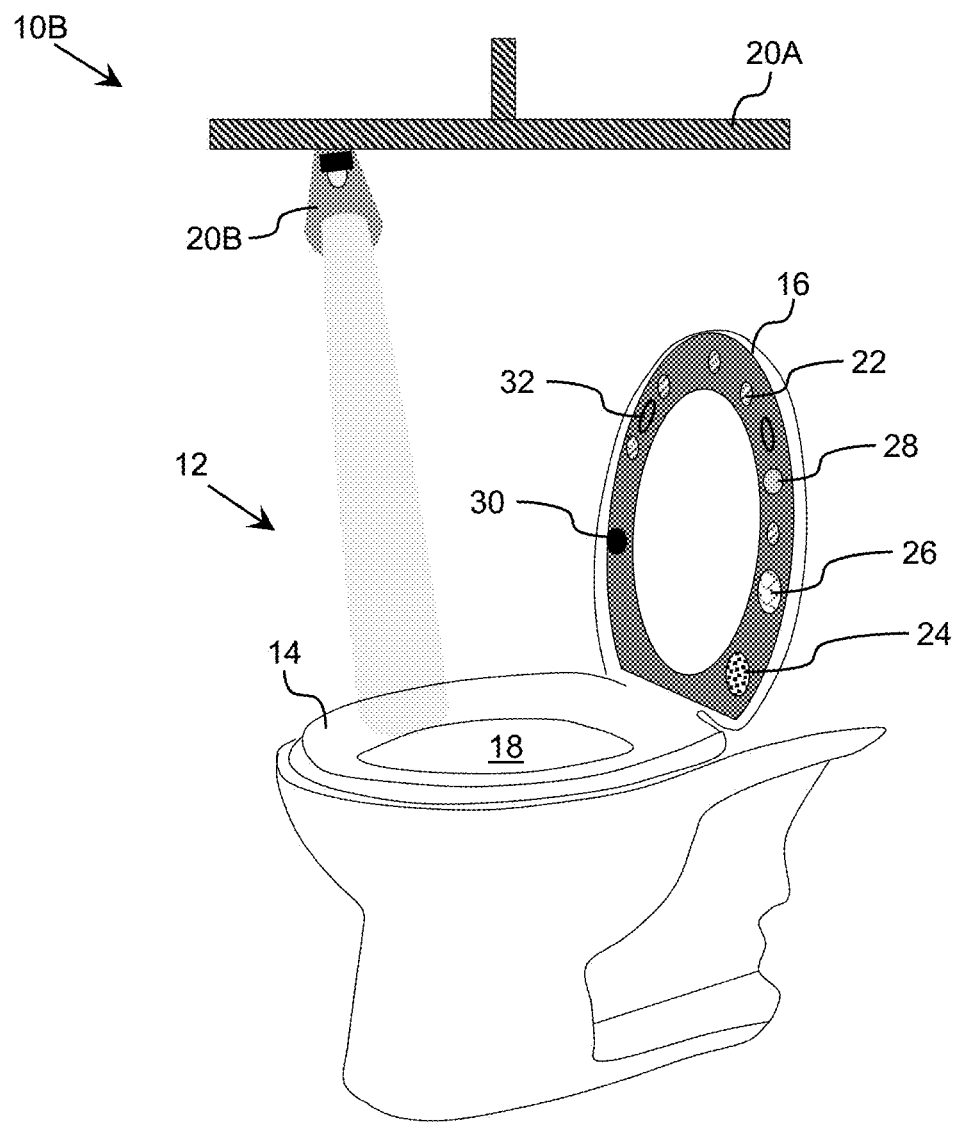

Turning to the drawings, FIGS. 1A and 1B show illustrative environments 10A, 10B, respectively, for cleaning one or more surfaces of a toilet 12 using ultraviolet radiation according to embodiments. As is known, a typical toilet 12 includes a seat 14 on which a user can sit while using the toilet 12 and a cover 16. As shown, the cover 16 can be selectively placed in a vertical position to allow the seat 14 to be exposed for use/cleaning, or a horizontal position which covers the seat 14 and bowl 18 of the toilet 12 when the toilet 12 is not being utilized and/or is being cleaned as described herein. Similarly, the seat 14 can be selectively placed in a vertical position, e.g., to allow the toilet 12 to be utilized without the seat 14, facilitate cleaning the seat 14 and/or bowl 18 of the toilet 12 as described herein, and/or the like.

In an embodiment, each environment 10A, 10B can include one or more ultraviolet sources 20A, 20B located near the toilet 12, which are capable of emitting ultraviolet radiation onto one or more surfaces of the toilet 12 in order to sterilize the surface(s). For example, the environment 10A is shown including a large ultraviolet source 20A, which is located above the toilet 12. The large ultraviolet source 20A can be configured to emit ultraviolet light directed onto various surfaces of the toilet 12, e.g., a top of the seat 14 and/or interior of the bowl 18 (when the cover 16 is in a vertical position), a top of the bowl 18 (when the seat 14 and cover 15 are in a vertical position), a flush mechanism (e.g., a tank lever, handle, button, and/or the like, operated by a user to cause the toilet 12 to flush), and/or the like. In an embodiment, a dosage and/or wavelength of the ultraviolet radiation is configured to prevent any microorganisms, such as bacteria, viruses, and/or the like, present on the surface(s) from growing beyond a target level. To this extent, the ultraviolet source 20A can be configured to emit a low intensity level of ultraviolet radiation in order to suppress growth and/or reproduction of the microorganisms present on exposed surface(s) of the toilet 12, such as bacteria, protozoa, and/or the like.

As illustrated in FIG. 1B, the environment 10B can include a focused ultraviolet source 20B, which can be configured to emit a focused beam of ultraviolet radiation that can be directed at one or more regions of an exposed surface of the toilet 12. In an embodiment, the focused ultraviolet source 20B is movable (e.g., rotatable and/or relocatable) to enable the beam of ultraviolet radiation to be directed at different regions of surface(s) of the toilet 12. For example, the focused ultraviolet source 20B can be moved to direct the ultraviolet beam to different regions of: the seat 14, a rim of the bowl 18 (e.g., when the seat 14 is in the vertical position), an interior of the bowl 18, a flush mechanism, and/or the like.

Additionally, one or both of the ultraviolet sources 20A, 20B can be configured to direct ultraviolet radiation onto other surfaces, e.g., in a bathroom. Illustrative surfaces include: a floor (e.g., around the toilet), a countertop, a sink, a shower/bath, faucet handles, a showerhead, a shower curtain or door, a door knob, a clothes hanger, a toilet paper holder, a waste bin, and/or the like. To this extent, an environment, such as a bathroom, can include any number of ultraviolet sources 20A, 20B, which are located and/or movable for directing ultraviolet radiation on any of various surfaces which are commonly handled by people, have standing water, are exposed to contaminants, and/or the like. To this extent, an environment can include one or more ultraviolet sources positioned above region(s) to be disinfected, such as the toilet, a shower, a sink, a tub, and/or the like, one or more ultraviolet sources located underneath in a position configured to direct ultraviolet radiation upward toward the region, such as near the floor in a location close to the toilet 12, on a surface near a faucet handle, and/or the like.

Each of the ultraviolet sources 20A, 20B can be formed of any combination of various ultraviolet sources. Illustrative ultraviolet sources include a high intensity ultraviolet lamp, such as a high intensity mercury lamp, an array of ultraviolet light emitting diodes (LEDs), and/or the like. In an embodiment, the focused ultraviolet source 20B comprises a movable ultraviolet source as shown and described in U.S. patent application Ser. No. 14/870,515, filed on 30 Sep. 2015, which is hereby incorporated by reference. In another embodiment, a handheld ultraviolet unit can be utilized to disinfect one or more of the various surfaces described herein. To this extent, an embodiment can include a handheld ultraviolet unit as shown and described in U.S. patent application Ser. No. 14/883,804, filed on 15 Oct. 2015, which is hereby incorporated by reference. In an embodiment, at least one ultraviolet source 20A, 20B includes at least one ultraviolet light emitting diode operating at a peak wavelength in a range of 250-280 nanometers.

Regardless, an embodiment provides a toilet 12 including one or more devices for sterilizing and/or cleaning one or more surfaces of the toilet 12. To this extent, the toilet 12 is shown having a cover 16 including various illustrative devices incorporated therein, which are configured to sterilize a top surface of the seat 14. These devices can include one or more of: an ultraviolet source 22 for emitting ultraviolet radiation for sterilizing a surface, a fluorescent source 24 for emitting ultraviolet radiation configured to excite a fluorescent signal from a target contaminant that may be present on the surface, a fluorescent sensor 26 for detecting the fluorescent signal and evaluating the fluorescence to determine a presence of the target contaminant on the surface, a visible light source 28 for illuminating the surface with visible light, and a visible light camera 30 for acquiring image data of the surface. While a particular arrangement of devices is shown, it is understood that this is only illustrative, and a cover 16 can include any number of each device, any combination of devices, and any arrangement of the devices. For example, an embodiment of a cover 16 can include one or more devices, such as ultraviolet sources 22, which are centrally located for directing ultraviolet radiation into the bowl 18. Similarly, a toilet 12 can include a seat 14 including an arrangement of one or more of the various devices 22, 24, 26, 28, which is configured to sterilize a rim of the bowl 18 using a similar solution as described herein in conjunction with the devices located on the cover 16. In an embodiment, the arrangement of devices is configured to provide data (e.g., fluorescent data, visible light data, and/or the like) regarding an entire lateral surface of the seat 14.

Furthermore, a toilet 12 can include various additional devices, which can be utilized to acquire similar data for evaluating a condition of the seat 14 and/or perform additional functionality as part of a cleaning and/or sterilization process. For example, a toilet 12 can include a reflectometer, which can be located on the cover 16 and utilized in conjunction with the visible light source 28 to acquire data corresponding to a reflectance of a surface illuminated by the visible light source 28. Such reflectance can be correlated with an amount of contamination present on the seat 14. In an embodiment, a set of visible light sources 28 capable of illuminating the seat 14 with multiple distinct visible wavelengths of light can be utilized to illuminate the seat 14 and acquire reflectance data for each of the distinct visible wavelengths. In an embodiment each wavelength can be chosen from blue, green and red colors, with understanding that different colors result in a better map of the surface contamination based on reflection data. Additionally, an embodiment can include a set of visible light sources 28 capable of illuminating the seat 14 at several irradiating angles and corresponding light reflection sensors. Illumination and reflection detection from different angles can provide more detailed reflection data for the surface. In an embodiment, the chosen angles may comprise a normal direction to the surface, as well as one or more of: a 15 degree, a 30 degree, a 45 degree a 60 degree and a 75 degree angle, with respect to the normal.

Similarly, the seat 14 can be coated with a conductive medium and an electrical conductivity of the conductive medium can be periodically measured. Illustrative materials for the conductive medium include conductive plastic, plastic incorporating a thin metallic mesh over a surface of the plastic, and/or the like. A change in the measured electrical conductivity can be used to determine a contamination of the seat 14. In either case, baseline measurements (e.g., reflectance, conductivity, and/or the like) can be acquired when the seat 14 is known to be clean. These baseline measurements can be used to correlate subsequent measurements acquired under the same conditions with an amount of contamination present on the seat 14.

As part of a cleaning and/or sterilization process described herein, the cover 16 can be lowered over the seat 14. In an embodiment, the cover 16 includes a mechanism, which is operable by a computer system to lower or raise the cover 16. To this extent, the computer system can automatically lower the cover 16 at the commencement of a cleaning and/or sterilization process and keep the cover 16 lowered until the cleaning and/or sterilization process is complete, at which time the computer system can raise the cover 16 and/or unlock the cover 16 to allow a user to raise the cover 16 when desired. The cover 16 can include a set of support elements 32 which are configured to maintain sufficient space between the devices located on the cover 16 and the top surface of the seat 14 for operation of the devices, e.g., to allow ultraviolet radiation to spread over substantially all of the top surface of the seat 14. For example, the cover 16 is shown including a set of support elements 32 protruding therefrom, which are configured to contact the top surface of the seat 14. In an embodiment, some or all of the set of support elements 32 are fabricated from an ultraviolet transparent material. In this case, ultraviolet radiation emitted by an ultraviolet source 22 can pass through the support element(s) 32 and irradiate the surface of the seat 14 located there under. However, it is understood that a cover 16 can include any of various alternative configurations for support element(s) 32.

In an embodiment, the cover 16 includes one or more optical elements (which can include one or more of the support elements 32), each of which can be located between at least one ultraviolet source 22 and the seat 14. The optical element can be configured to scatter and diffuse the ultraviolet radiation emitted by the ultraviolet source(s) 22 prior to the ultraviolet radiation impacting the seat 14. Such optical element(s) can provide a more uniform distribution and/or a larger surface area of illumination on the surface of the seat 14. Illustrative optical elements include, but are not limited to, lenses, diffusive transparent surfaces, flat and curved mirrors, TIR lenses, and/or the like.

In an embodiment, a toilet 12 includes an integrated system for cleaning (e.g., washing and/or drying) one or more surfaces of the toilet 12, such as the top surface of the seat 14, the rim and/or interior of the bowl 18, and/or the like. When implemented in conjunction with a sterilization system, the toilet 12 and/or the surrounding environment provides a solution for providing a clean, sterilized toilet 12 for use by various individuals.

Figure 2A:
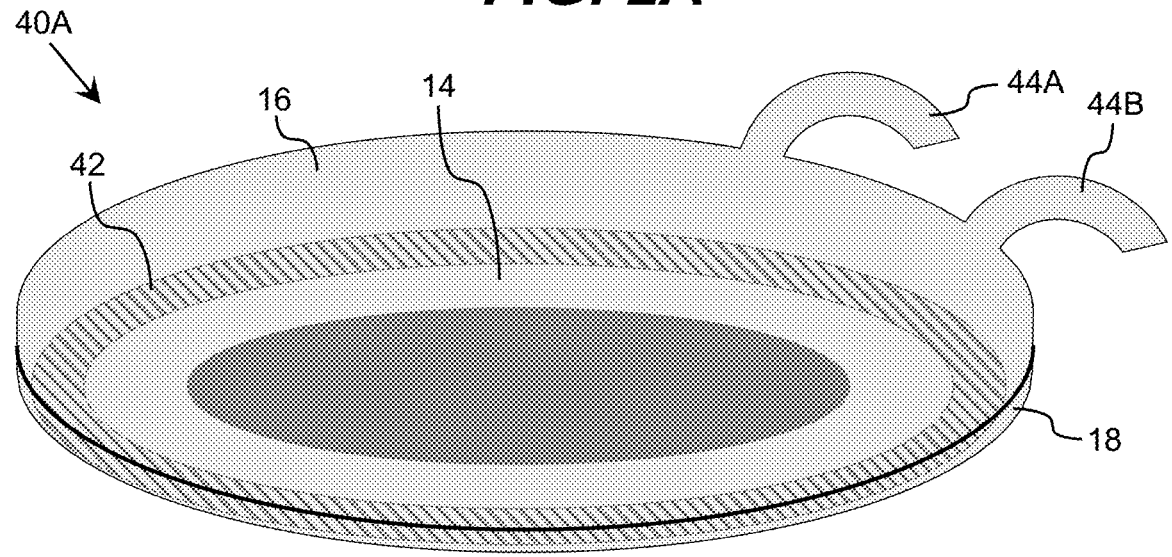
FIGS. 2A and 2B show a perspective view and a side cross section view of toilet seat cleaning systems according to embodiments.
Figure 2B:
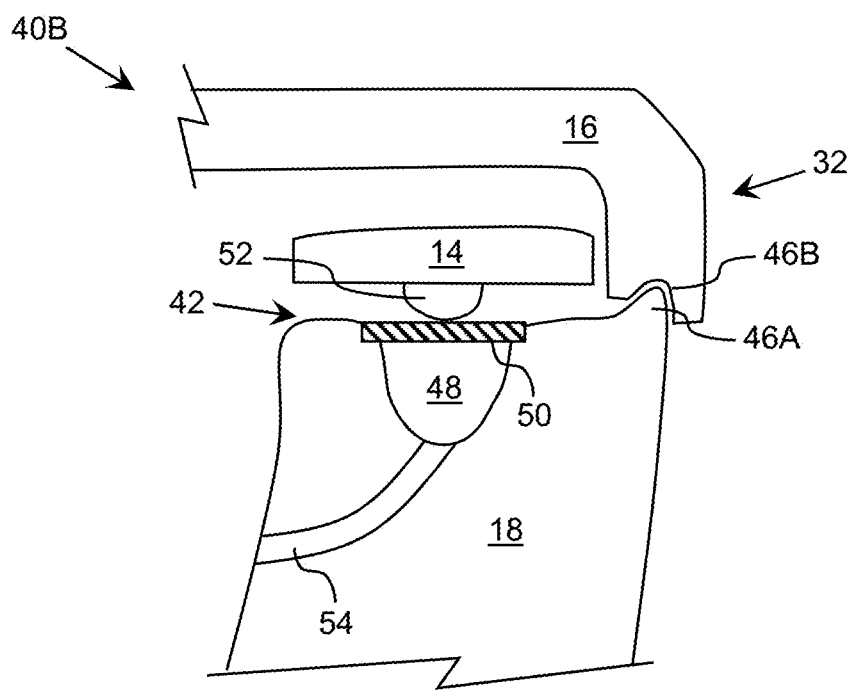

FIGS. 2A and 2B show a perspective view and a side cross section view of toilet seat cleaning systems 40A, 40B according to embodiments. In FIG. 2A, the toilet seat cleaning system 40A is shown including a bowl 18 having a support surface 42 (indicated by diagonal lines), which is configured to support the seat 14 when in a horizontal position. The support surface 42 can be slightly larger in size than the seat 14 and include means for forming a watertight coupling with the cover 16 when closed. Furthermore, the support surface 42 can include means for collecting water and other debris, which is used to clean the seat 14 and/or support surface 42 of the bowl 18. The cover 16 can include a set of fluid sources 44A, 44B, through which a liquid, such as water, a cleaning fluid, and/or the like, can flow to clean the seat 14 and/or bowl 18.

FIG. 2B shows further details of an illustrative outer portion of a toilet seat cleaning system 40B according to an embodiment. As illustrated, the cover 16 can be configured to attach to the support surface 42 in a watertight manner. For example, the support surface 42 is shown including an outer lip 46A, which can be located beyond the outer edge of the seat 14 and to which a support element 32 of the cover 16 can be attached. As illustrated, the support element 32 of the cover 16 can include a corresponding groove 46B, which is sized and located to form a watertight seal along the outer edge of the bowl 18, surrounding the seat 14. In this case, the support element 32 of the cover 16 can be sized to hold the cover 16 a target distance from the top surface of the seat 14 to facilitate cleaning and/or sterilizing at least the top surface of the seat 14.

The support surface 42 of the bowl 18 also can be configured to collect the fluid utilized to clean the seat 14. To this extent, as shown in FIG. 2B, the support surface 42 can include a cavity 48, which can be enclosed by a mesh structure 50. The mesh structure 50 can be supported by opposing sides of the cavity 48 and, in turn, can support the seat 14, e.g., via a set of support elements 52 located on an underside of the seat 14 and protruding therefrom. In this case, the mesh structure 50 must be formed of a material having sufficient strength to hold the weight of a user sitting on the seat 14. Illustrative materials for the mesh structure 50 include a steel or aluminum mesh having an appropriate thickness to provide the required strength. In an alternative embodiment, the seat 14 can include multiple support elements 52 arranged to contact the support surface 42 on opposing sides of the cavity 48. Regardless, the bowl 18 can include a set of channels 54 formed therein, which extend from the cavity 48 to an interior of the bowl 18. The channel(s) 54 can drain the fluid from the channels 54 into the bowl 18, and the fluid can subsequently be flushed from the bowl 18 after cleaning has completed.

A cleaning cycle can be initiated using any solution. For example, a cleaning cycle can be initiated automatically, e.g., in response to: the cover 16 being lowered over the seat 14; passage of a preset amount of time; after a preset number of uses; in response to a request from a user (e.g., through activation of a cleaning request mechanism, such as a pedal on the floor); and/or the like. During the cleaning cycle, a cleaning fluid can flow through the fluid sources 44A, 44B, be distributed around the surface of the seat 14 to clean the seat 14, and flow into the interior of the bowl 18 and/or the cavity 48 and cannel(s) 48 for disposal. Feedback regarding a need for the cleaning and/or an effectiveness of the cleaning can be acquired, for example, by a visible light camera 30 (FIG. 1A), which can obtain image data suitable for measuring a reflectivity of the surface of the seat 14. The reflectivity can indicate a cleanliness of the seat 14.

Figure 3A:
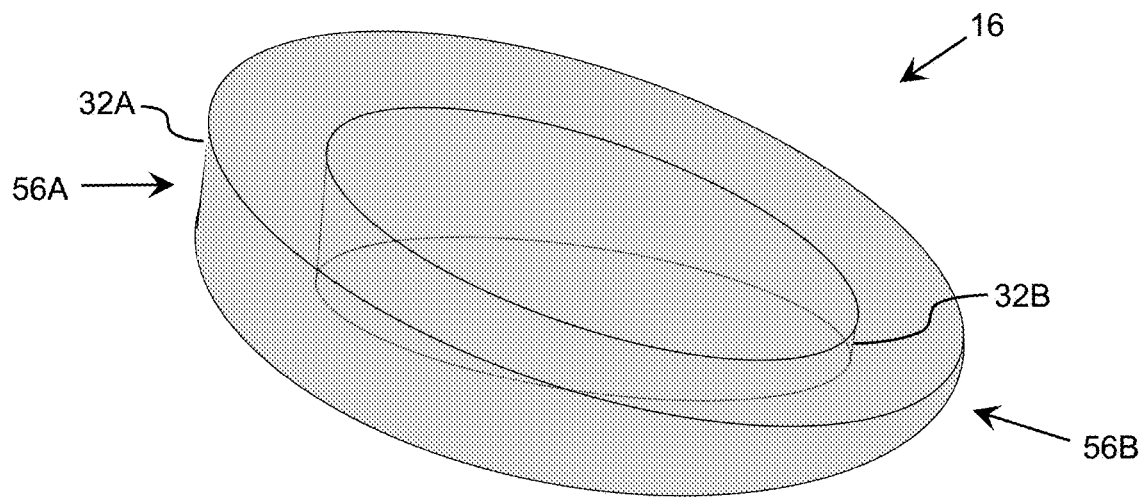
FIGS. 3A and 3B show views of an illustrative cover according to an embodiment.
Figure 3B:
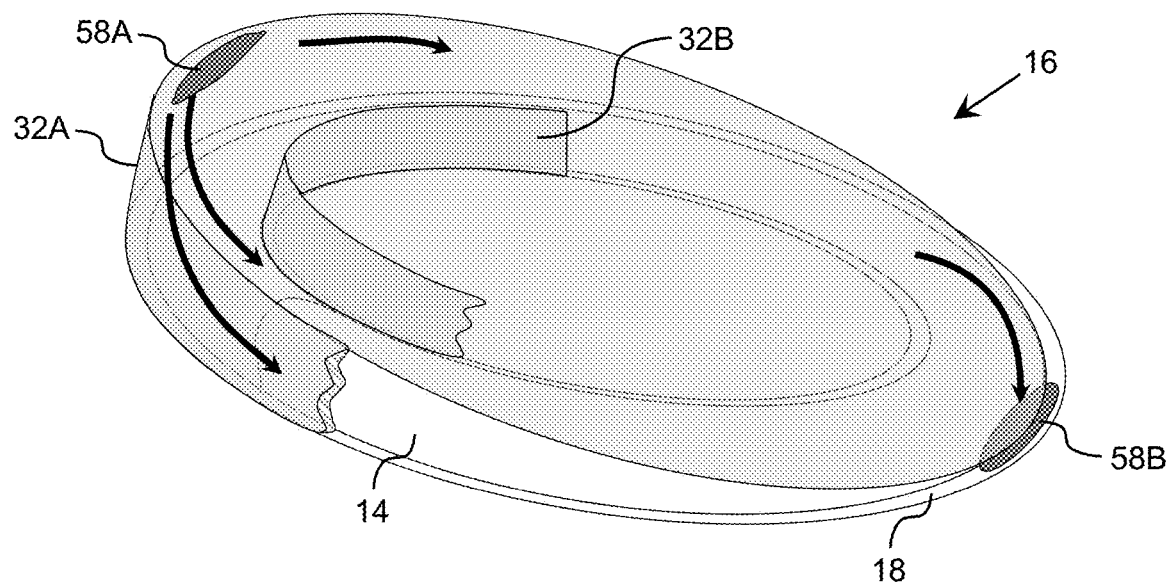

In an embodiment, the cover 16 and bowl 18 can be configured to form a watertight connection on both the exterior and interior sides of the seat 14 to form a channel within which the seat 14 is located and fluid can flow during a cleaning cycle. To this extent, FIGS. 3A and 3B show views of an illustrative cover 16 according to an embodiment. As shown in FIG. 3A, the cover 16 can include an outer support element 32A and an inner support element 32B. Each support element 32A, 32B can be configured to form a watertight seal with the bowl 18 (FIG. 2B) using any solution, e.g., a lip and groove as described herein. Furthermore, the support elements 32A, 32B of the cover 16 can have a varying thickness. To this extent, the cover 16 can have a thick side 56A and a thin side 56B with a gradually sloping top surface. However, it is understood that this is only illustrative of various possible configurations for the cover 16. The varying thickness can be configured to, for example, adjust one or more aspects of the flow of a cleaning fluid. In an embodiment, the thickness of the cover can range from 1 cm-50 cm on the thick side 56A and from 0.5 cm to 20 cm on the thin side 56B. The pressure and the velocity of the fluid flow can be configured to be sufficient to dislodge typical debris that can be found on the seat 14 and wash it out. In an embodiment, the fluid sources 44A, 44B can include high pressure jets, where the pressure is selected to dislodge debris found on the toilet seat without causing damage to the toilet seat.

As shown in FIG. 3B, during a cleaning cycle, a cleaning fluid, such as water, can enter the channel formed by the cover 16 through an inlet 58A and flow around the seat 14 before exiting through an outlet 58B located in the bowl 18. The inlet 58A and outlet 58B can be located to provide cleaning of an entire surface of the seat 14. Furthermore, a fluid pressure and/or turbulence levels, which can be at least partially created by the varying thickness of the cover 16, can be configured to provide a target level of cleaning for the seat 14. After completion of the fluid cleaning cycle, an embodiment can further introduce flowing air, such as heated air, into the channel formed by the cover 16, e.g., via the inlet 58A and/or the outlet 58B, to facilitate drying of the seat 14.

Figure 4A:
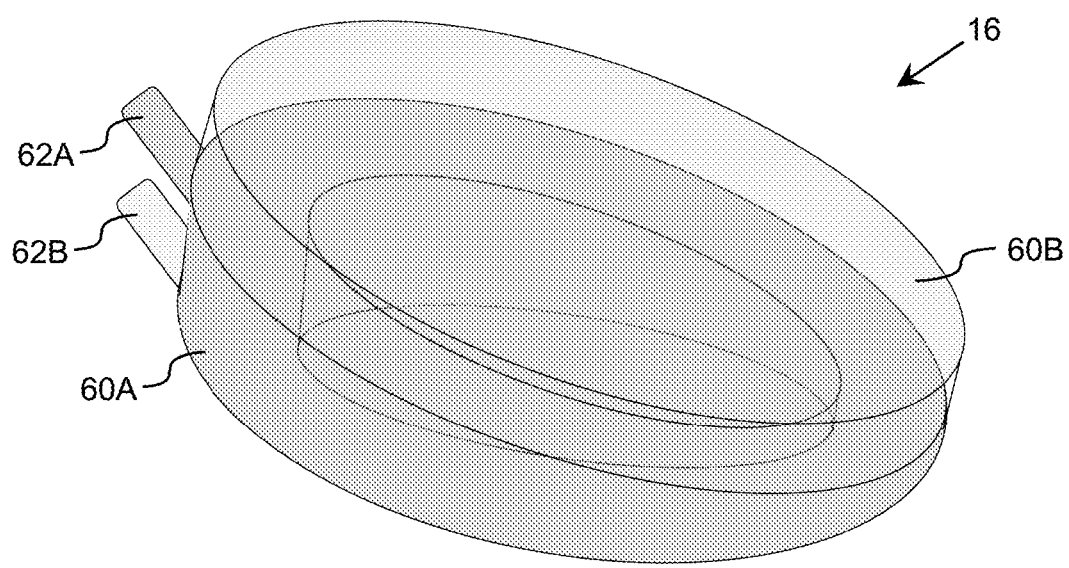
FIGS. 4A and 4B show views of an illustrative cover according to another embodiment.
Figure 4B:
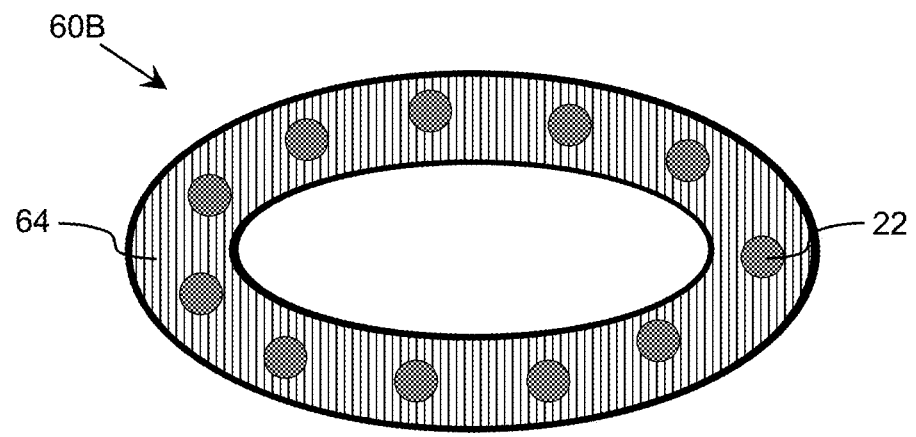

A cover described herein can be configured for both ultraviolet sterilization and cleaning of a corresponding seat. To this extent, FIGS. 4A and 4B show views of an illustrative cover 16 according to an embodiment. In this case, the cover 16 includes two sections 60A, 60B. A first section 60A can be configured to form a channel for fluid-based cleaning and air drying as described herein. To this extent, the first section 60A is shown including a fluid inlet 62A for introducing a fluid into the channel formed by the first section 60A, and an air inlet 62B for introducing air into the channel.

As shown in FIG. 4B, the second section 60B can house a set of devices, including ultraviolet sources 22, for sterilizing the seat located adjacent to the first section 60A of the cover 16. The devices included in the second section 60B can be separated from the channel using any solution. In an embodiment, the second section 60B comprises an ultraviolet transparent material 64, which defines the boundary between the first and second sections 60A, 60B and forms a top surface of the channel formed by the first section 60A. The devices included in the second section 60B can be located on an opposite side of the ultraviolet transparent material 64 as the channel and/or embedded in the ultraviolet transparent material 64. In this manner, the devices in the second section 60B can be isolated from the channel and/or ambient, thereby avoiding contamination. The ultraviolet transparent material 64 can be formed of any suitable material. In an embodiment, the ultraviolet transparent material 64 comprises an ultraviolet transparent polymer, such as a fluoropolymer. However, other materials can be utilized including, for example, fused silica, sapphire, anodized aluminum oxide (AAO), and/or the like.

Furthermore, the ultraviolet transparent material 64 can form a light guiding structure, which is configured to distribute the ultraviolet radiation and/or visible light emitted from the devices located in the second section 60B. For example, the light guiding structure can diffuse the ultraviolet radiation emitted by the ultraviolet sources 22, direct the ultraviolet radiation to one or more locations, focus the ultraviolet radiation, and/or the like. In an embodiment, the second section 60B can include an ultraviolet transparent light guiding structure 64 fabricated using a solution as described in U.S. patent application Ser. Nos. 14/853,057 and/or 14/853,014, both of which were filed on 14 Sep. 2015 and both of which are hereby incorporated by reference. A diffusive ultraviolet source is shown and described in U.S. patent application Ser. No. 14/853,075, filed on 14 Sep. 2015, which is hereby incorporated by reference.

In an embodiment, the second section 60B includes a set of ultraviolet transparent windows formed of the ultraviolet transparent material. In this case, a remaining portion of the second section 60B at the interface between the first and second sections 60A, 60B can be formed of another material, such as an ultraviolet reflective material, an ultraviolet absorbing material, and/or the like. The ultraviolet transparent window(s) can have a size, shape, and/or location selected to enable delivery of ultraviolet radiation to a desired location on an adjacent seat. Furthermore, as described herein, the second section 60B can include additional devices, such as a fluorescent ultraviolet source, a visible light source, a camera, a fluorescent sensor, and/or the like, which can be located and configured to direct radiation to and/or sense radiation from the surface of the seat.

Regardless, the second section 60B can include one or more layers/materials to manage propagation of the ultraviolet radiation emitted by the ultraviolet sources 22. To this extent, an outer layer of the second section 60B can comprise a material reflective of ultraviolet radiation. For example, the outer layer can include at least an inner surface formed of the reflective material. Illustrative ultraviolet reflective materials include, but are not limited to a fluoropolymer film, an aluminum film, a multilayer polymer film that includes a reflective polymer (e.g., Teflon), a multilayer polymer film that includes an aluminum film, a diffusively reflective material, such as a highly ultraviolet reflective expanded polytetrafluoroethylene (ePTFE) membrane (e.g., GORE® Diffuse Reflector Material), and/or the like.

Figure 5A:
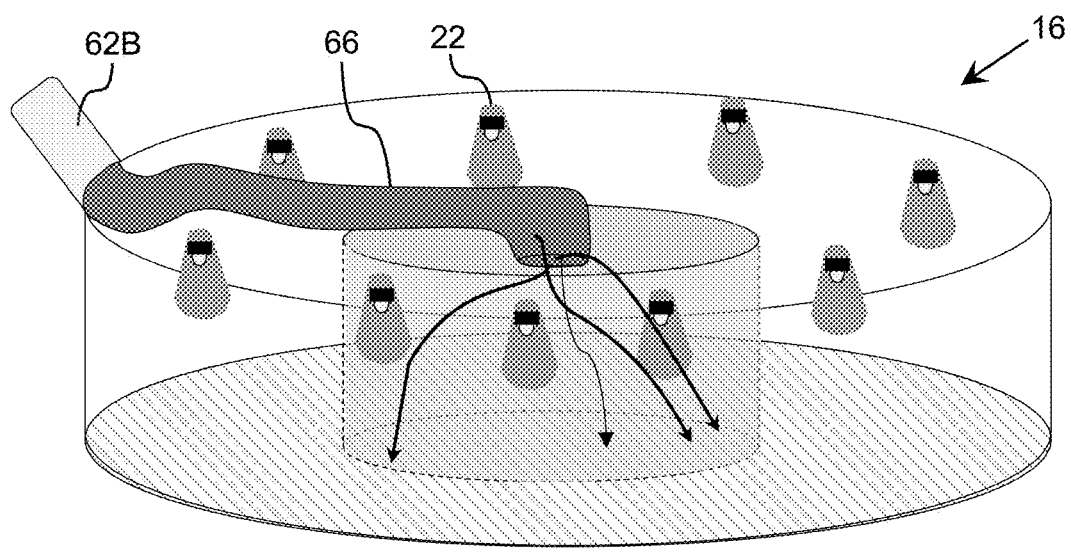
FIGS. 5A-5C show views of other illustrative covers according to embodiments.
Figure 5B:
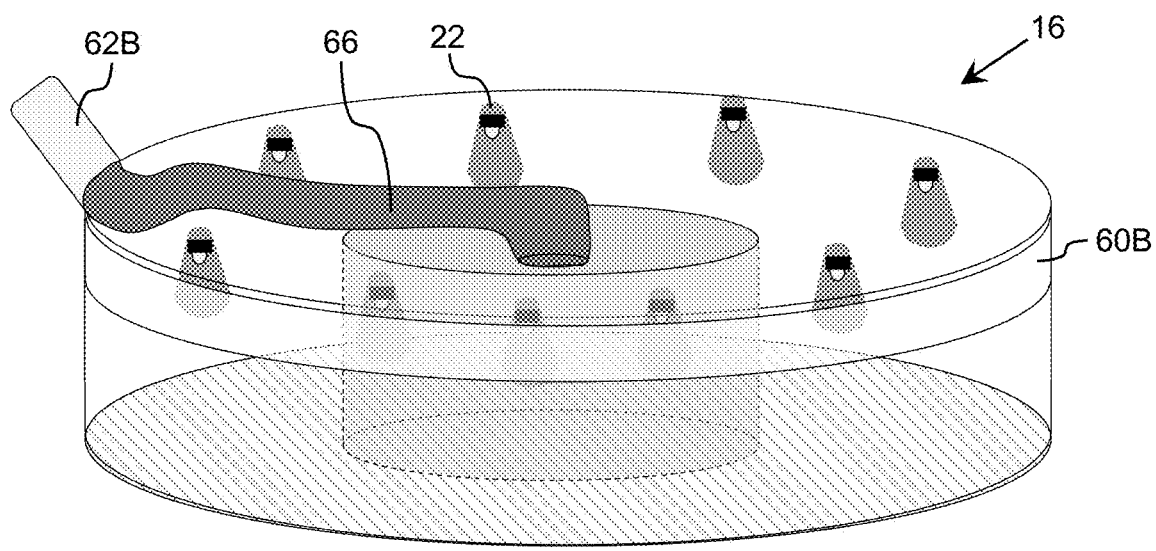
Figure 5C:
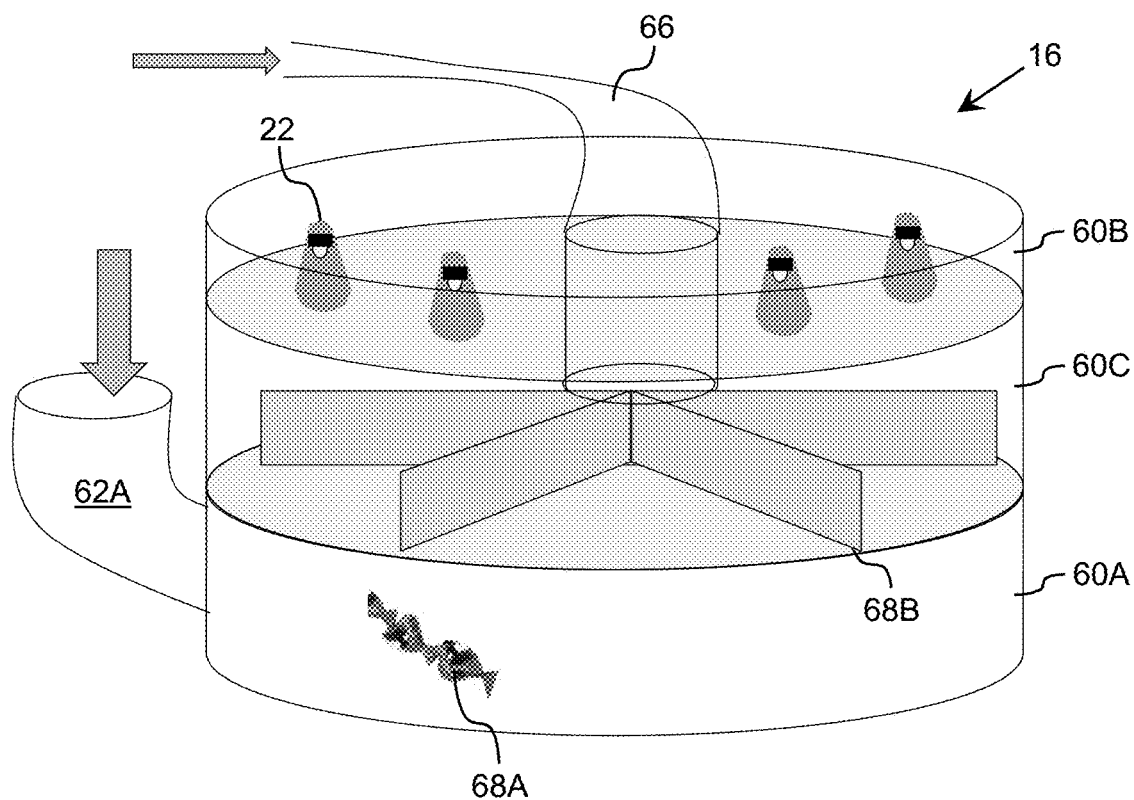

It is understood that various alternative configurations of the cover 16 can be implemented in embodiments. For example, FIGS. 5A-5C show views of other illustrative covers 16 according to embodiments. In FIG. 5A, the cover 16 includes a plurality of ultraviolet sources 22, e.g., movable focused ultraviolet sources, located around a perimeter of the cover 16. The ultraviolet sources 22 can have an arrangement and spacing configured to direct ultraviolet radiation onto substantially all of a surface of an adjacent seat. Furthermore, the cover 16 can include an air inlet 62B, which can introduce air into the region between the cover 156 and the seat. As illustrated, the air inlet 62B can be fluidly connected to an air pipe 66, which delivers the air to a central region of the cover 16. As illustrated, the air, such as heated air, can exit the air pipe 66 in the central region and circulate over the corresponding seat. In FIG. 5B, the ultraviolet sources 22 are located within a second section 60B, which can be configured to provide light guiding and/or protection of the ultraviolet sources 22 from contamination and/or the heat of the air delivered through the air pipe 66. Furthermore, the second section 60B can be configured to provide light guiding of the ultraviolet radiation. Regardless, as shown in FIGS. 5A and 5B, the arrangement of ultraviolet sources 22 can be spatially separated from the air outlet to prevent degradation of the ultraviolet sources 22 due to use of heated air.

In FIG. 5C, the cover 16 includes three sections 60A-60C. As described herein, the section 60A can be located directly adjacent to a seat and include a fluid inlet 62A for washing the seat with a cleaning fluid, such as water. Additionally, the section 60B can include an ultraviolet transparent and/or light guiding material and include a set of ultraviolet sources 22 for directing ultraviolet radiation onto the surface of the seat as part of a sterilization process. Furthermore, the cover 16 is shown in including a section 60C located between the sections 60A, 60B in which air is introduced onto a surface of the seat from the air pipe 66.

In an embodiment, one or more of the sections 60A-60C can include a set of mixing elements for creating turbulence and/or ensuring mixing of the corresponding treatment. For example, the section 60A can include a set of mixing elements 68A, which can be operated and/or placed to create turbulence in the flow of the cleaning fluid entering from the fluid inlet 62A. Similarly, the section 60C can include a fan 68B, which can circulate the air exiting the air pipe 66. Furthermore, as discussed herein, the section 60B can include a wave guiding structure and/or diffusive light emitter to ensure a more even distribution of ultraviolet radiation onto the surface of the seat.

As described herein, embodiments provide a solution for sterilizing a seat of a toilet when the cover is up and/or when the cover is down in a typical operating configuration of a toilet seat and cover. Furthermore, embodiments provide for cleaning the seat of debris when the cover is down. However, it is understood that embodiments can perform such cleaning and/or sterilizing in another configuration of the seat and/or cover.

Figure 6A:
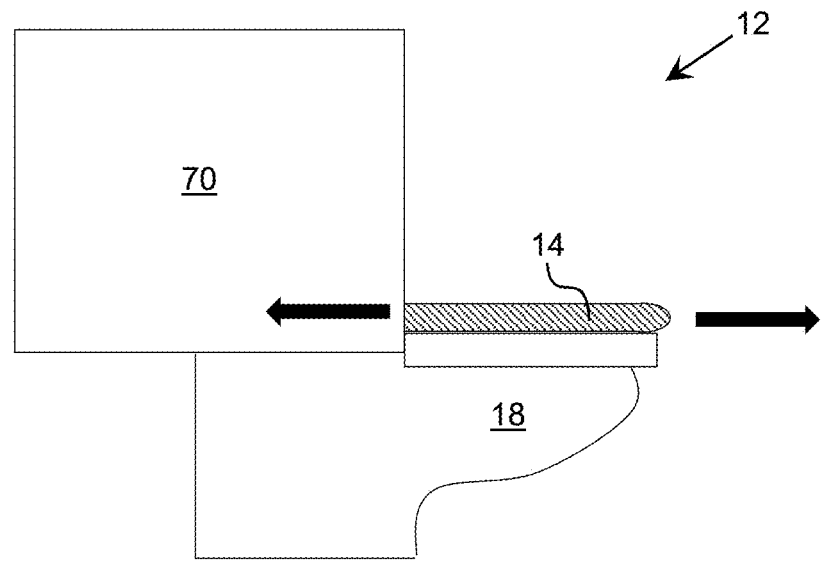
FIGS. 6A and 6B show alternate configurations of an illustrative toilet including a cleaning chamber according to an embodiment.
Figure 6B:
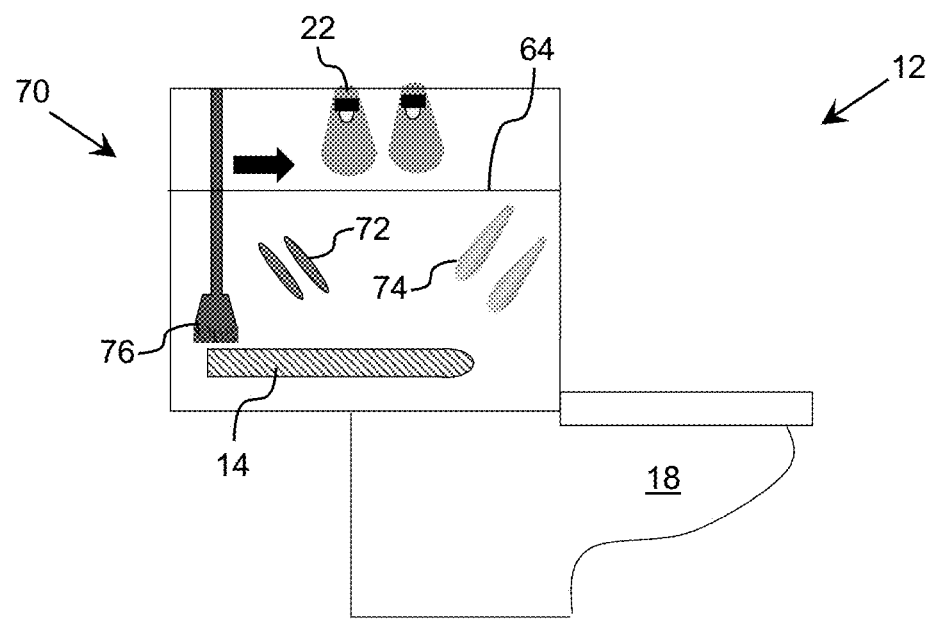

For example, FIGS. 6A and 6B show alternate configurations of an illustrative toilet 12 including a cleaning chamber 70 according to another embodiment. As shown in FIG. 6A, the seat 14 can be located over a bowl 18 to enable use of the toilet 12 by a user. However, the seat 14 can be horizontally slid into/out of the cleaning chamber 70 located on a back of the toilet 12 using any solution. In an embodiment, the seat 14 is mounted to a railing installed underneath the seat 14, and the toilet 12 can include a motor capable of pulling the seat 14 to slide the seat 14 in and push the seat 14 to slide the seat out. The seat 14 can be accompanied by rollers capable of rolling along the railing. Pushing the seat 14 can be accomplished by a spring, while pulling the seat 14 can be accomplished by a belt connected to a rotating motor. Other mechanical configurations known in art are possible as well. The cleaning chamber 70 can include a door or other mechanism, which allows the seat 14 to be slid therein as well as provides a watertight seal when the seat 14 is located within the cleaning chamber 70.

Within the cleaning chamber 70, as shown in FIG. 6B, the toilet 12 can include any combination of various devices for cleaning/sterilizing the seat 14. For example, the cleaning chamber 70 can include a set of ultraviolet sources 22, which can be located behind/within ultraviolet transparent material 64. Furthermore, the cleaning chamber 70 can include a set of fluid sources 72 (e.g., for delivering high pressure water) and/or a set of air sources 74 (e.g., for delivering high pressure hot air). The cleaning chamber 70 also can include a wet brush 76, which can be movable along a horizontal direction indicted by the arrow to physically clean a top surface of the seat 14. The wet brush 76 can move through the use of railing installed adjacent to the wet brush 76 and a motor capable of pulling the wet brush 76 in a forward or backward direction. The wet brush 76 can comprise rollers capable of rolling along the railing. It is understood that the particular combination and arrangement of devices is only illustrative of numerous possible arrangements and combinations of devices which can be implemented in embodiments to sterilize and/or clean the seat 14 within a cleaning chamber 70.

Figure 7A:
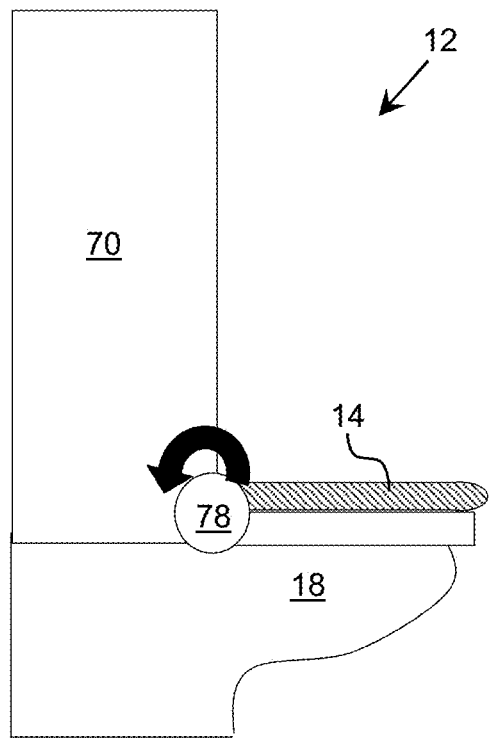
Figure 7B:
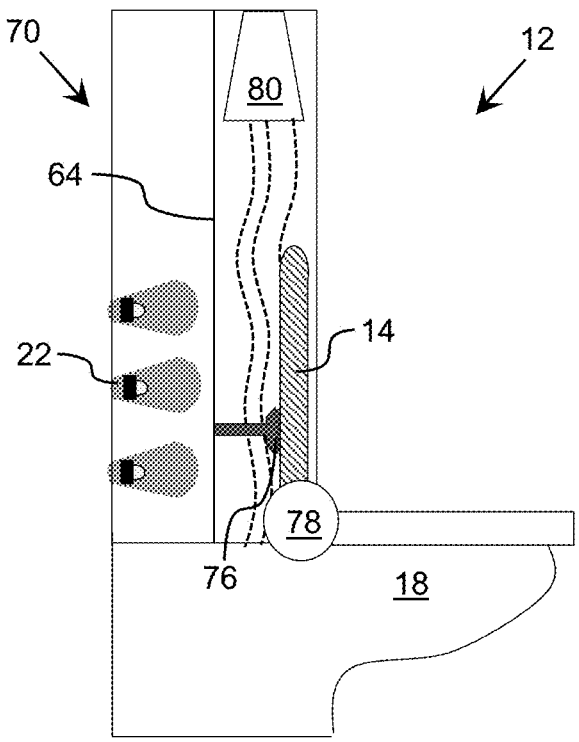

Alternatively, the seat 14 can be rotated into/out of a cleaning chamber 70. To this extent, FIGS. 7A and 7B show alternate configurations of another illustrative toilet 12 including a cleaning chamber 70 according to an embodiment. As shown in FIG. 7A, the seat 14 can be located over a bowl 18 to enable use of the toilet 12 by a user. However, the seat 14 can be rotated to a horizontal position, which is within the cleaning chamber 70 located on a back of the toilet 12 using any solution, e.g., a hinged connection mechanism 78. The cleaning chamber 70 can include a door or other mechanism, which allows the seat 14 to be rotated therein as well as provides a watertight seal when the seat 14 is located within the cleaning chamber 70.

Within the cleaning chamber 70, as shown in FIG. 7B, the toilet 12 can include any combination of various devices for cleaning/sterilizing the seat 14. For example, the cleaning chamber 70 can include a set of ultraviolet sources 22, which can be located behind/within ultraviolet transparent material 64. Furthermore, the cleaning chamber 70 can include a fluid source 80, which can supply a cleaning fluid, such as water, air, and/or the like, which is directed downward and over the seat 14. In an illustrative embodiment, the fluid source 80 can be equipped with jets of high pressure water for cleaning the seat 14. The ultraviolet sources 22 and/or other devices (e.g., sensors of fluorescent signal, sources for excitation of such signal, visible light sources, cameras, and/or the like) can be physically separated from the seat 14 and the fluids emitted by the fluid source 80 by the ultraviolet transparent material 64.

Figure 7C:
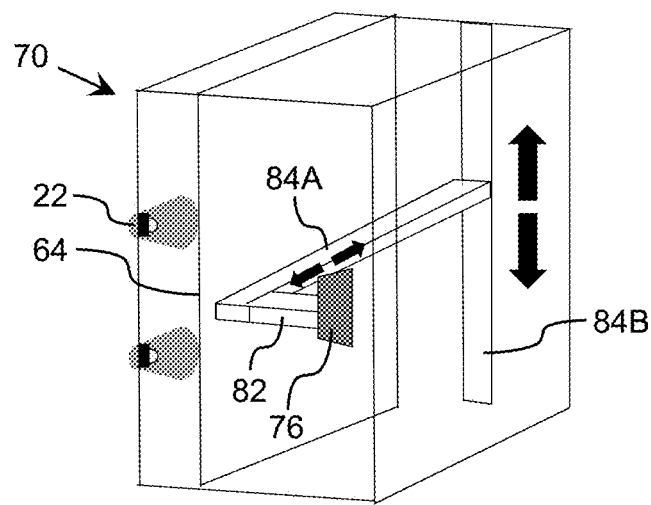
FIG. 7C shows further details of an illustrative wet brush included in the cleaning chamber according to embodiments.

Additionally, the cleaning chamber 70 can include a wet brush 76, which is operable to physically clean at least a top surface of the seat 14. The wet brush 76 described herein can be configured to prevent obscuring ultraviolet light emitted by the ultraviolet sources 22. To this extent, FIG. 7C shows further details of an illustrative wet brush 76 included in the cleaning chamber 70 according to embodiments. As illustrated, the wet brush 76 can be connected to an arm 82, which is further connected to a first railing system 84A. The first railing system 84A can enable horizontal movement of the wet brush 76 using any solution. Additionally, the first railing system 84A can be connected to a second railing system 84B, which is operable to move the first railing system 84A in a vertical direction. In this manner, the wet brush 76 can be selectively moved to any location within a rectangular region defined by the railing systems 84A, 84B. With such an arrangement, the brush 76 can be slid towards the upper or lower side of the cleaning chamber 70 when not in use to prevent obscuring ultraviolet light emitted by the ultraviolet sources 22. It is understood that the railing systems 84A, 84B are only illustrative of different solutions for moving the wet brush 76, which can be implemented in a cleaning chamber 70 described herein.

In an embodiment, some or all of the ultraviolet and/or visible light components can be removable for repair, replacement, and/or cleaning. For example, embodiments described herein can include an ultraviolet transparent material 64 that is physically removable. In this manner, the ultraviolet transparent material 64 can be cleaned and reinserted, replaced, and/or the like. Furthermore, after removing the ultraviolet transparent material 64, a user can access the devices, such as the ultraviolet sources 22, located there behind. In this manner, one or more of the devices can be repaired, cleaned, replaced, and/or the like.

Figure 8:
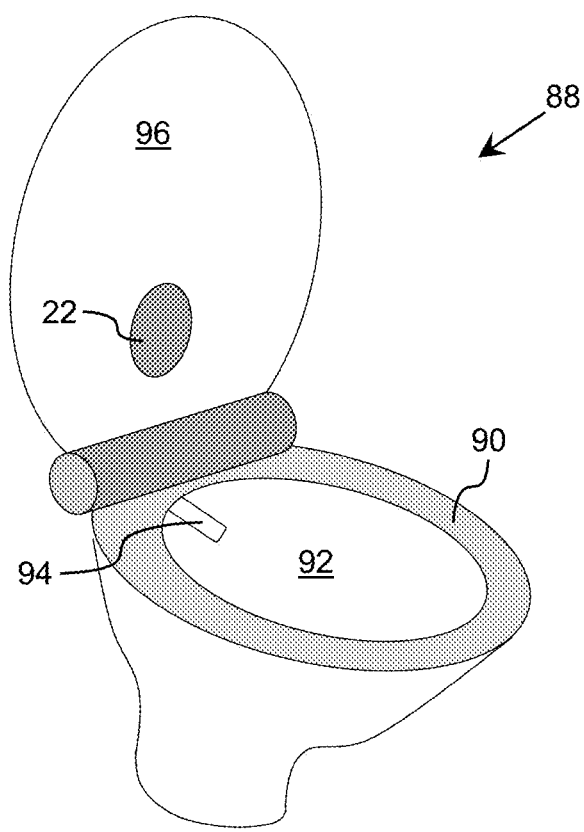
FIG. 8 shows a bidet according to an embodiment.

As discussed herein, a toilet is only illustrative of various bathroom fixtures which can include a set of devices for ultraviolet sterilization and/or cleaning as described herein. Other illustrative bathroom fixtures include a faucet, a faucet handle, a showerhead, a shower, a bath, and/or the like. Furthermore, embodiments can be implemented in conjunction with bathroom fixtures similar in configuration to a toilet. For example, an embodiment provides a system for sterilizing and/or cleaning a urinal. FIG. 8 shows a bidet 88 according to an embodiment. The bidet 88 includes an ultraviolet source 22, which can be configured to sterilize a rim 90, a bowl 92, a nozzle 94, and/or the like, of the bidet 88. For example, the ultraviolet source 22 can be located on a rotatable cover 96 of the bidet 88, which can be configured similar to the covers for toilets described herein. Additionally, one or more ultraviolet sources 22 can be located in alternative locations. For example, the nozzle 94 can include a set of ultraviolet sources located thereon, which are configured to sterilize one or more surfaces of the nozzle 94 when not in use.

In any of the embodiments described herein, an ultraviolet source can include at least one ultraviolet source operating in the UV-C wavelength range and at least one ultraviolet source operating in the blue-ultraviolet wavelength range of 380 nm to 420 nm. In an embodiment, the blue-ultraviolet sources can be high intensity, wide coverage sources that are capable of continuous operation over a large span of time. For example, the blue-ultraviolet radiation source can operate continuously for several days. Prolonged exposure to radiation in the blue-ultraviolet wavelength range results in sterilization due to the generation of reactive oxygen species (ROS). ROS are chemically reactive chemical species that contain oxygen. The ROS can disrupt the proliferation of microorganisms by binding to and oxidizing the microorganisms.

It is understood that both the UV-C sources and the blue-ultraviolet sources can produce a distributed intensity over one or more areas that are located a distance away from the sources. In an embodiment, the distance between the sources and the target can range from a few centimeters to several meters. In an embodiment, irradiation of a location defines a region of the target area that is impinged by radiation, wherein the intensity of radiation deposited at the boundary of the region is at most 10% of the intensity of light deposited at the center of the region. It is understood that the position of irradiated locations can be adjusted to result in separate locations over the surface of the target area, wherein separate means that the intensity of radiation between each of the locations is no larger than 10% of the intensity in the center of the locations. In addition, these locations of irradiation can be designed to have relatively uniform radiation, with radiation intensity varying through the location by no more than several times (e.g., a factor of three or less) between any two points within the location.

The UV-C sources and the blue-ultraviolet sources can comprise any combination of one or more ultraviolet radiation emitters. Examples of an ultraviolet radiation emitter can include, but are not limited to, high intensity ultraviolet lamps (e.g., high intensity mercury lamps), discharge lamps, ultraviolet LEDs, super luminescent LEDs, laser diodes, and/or the like. In one embodiment, the ultraviolet radiation source can include a set of LEDs manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the ultraviolet radiation source can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures can include, but are not limited to, a wave guide, a plurality of ultraviolet fibers, each of which terminates at an opening, a diffuser, and/or the like.

As described herein, in any of the embodiments, the ultraviolet source can include at least one ultraviolet source operating in the UV-C wavelength range and at least one ultraviolet source operating in the blue-ultraviolet wavelength range. It is also understood that in any of the embodiments, the ultraviolet sources can include a set of ultraviolet radiation sources each operating at a different peak wavelength (A). In an embodiment, each of the ultraviolet radiation sources can irradiate a different location of the surface of the seat. In an embodiment, the ultraviolet radiation sources can irradiate each location with relatively uniform radiation. In another embodiment, more than one ultraviolet radiation source can be used to irradiate a single location on the surface, with each irradiating the common location at a different intensity of radiation.

Each of the UV-C sources can be configured to emit radiation at a specific wavelength selected from a range extending from 250 nm to 360 nm. In general, for adequate optimization of the irradiation that is provided by the ultraviolet radiation sources, the wavelength range can be selected to be significantly narrower, depending on the type of microorganisms being sterilized. For instance, the wavelength range can extend from 270 nm to 320 nm, and in some cases, depending on the optimization target, the range can extend from 280 nm to 300 nm, or from 260 nm to 280 nm. In one embodiment, the ultraviolet radiation sources can have a peak wavelength that ranges from 270 nm to 300 nm. In another embodiment, the ultraviolet radiation sources can have a peak wavelength of 295 nm with a full width half maximum of 10 nm.

In order to facilitate the efficiency of irradiation performed by the UV-C radiation sources, a set of reflective optical elements can be used to focus the ultraviolet radiation to locations on the toilet seat surface. In one embodiment, each optical element can be configured to focus ultraviolet radiation emitted from one of the ultraviolet radiation sources to a respective location on the surface. Examples of optical elements that can be used in conjunction with the ultraviolet radiation sources include, but are not limited to, a lens and/or a set of lenses.

Figure 9A:
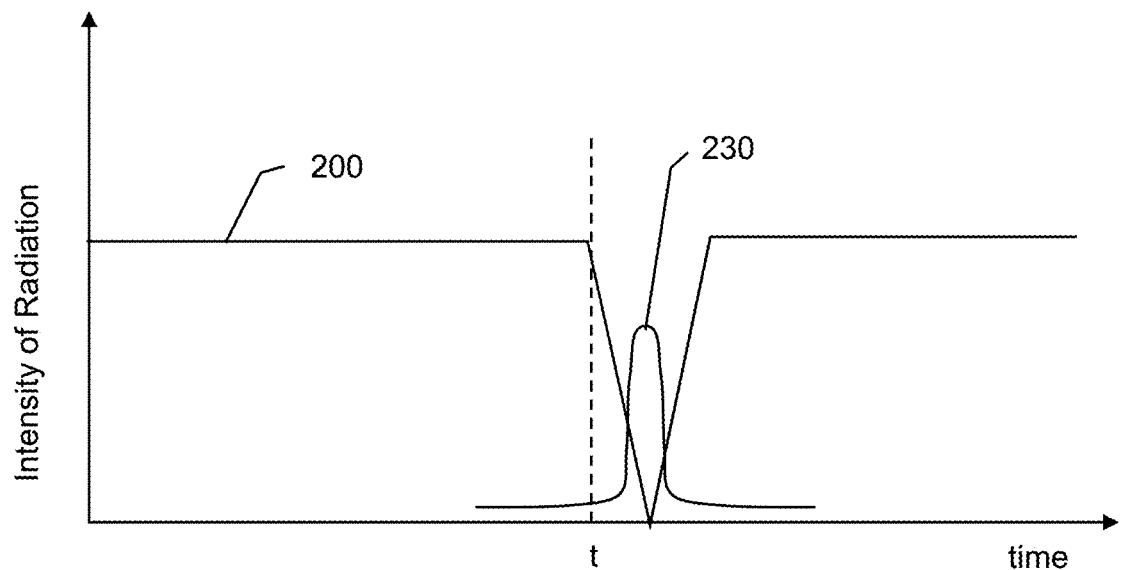
FIGS. 9A and 9B show graphical examples depicting the operation of an illustrative toilet according to an embodiment.
Figure 9B:
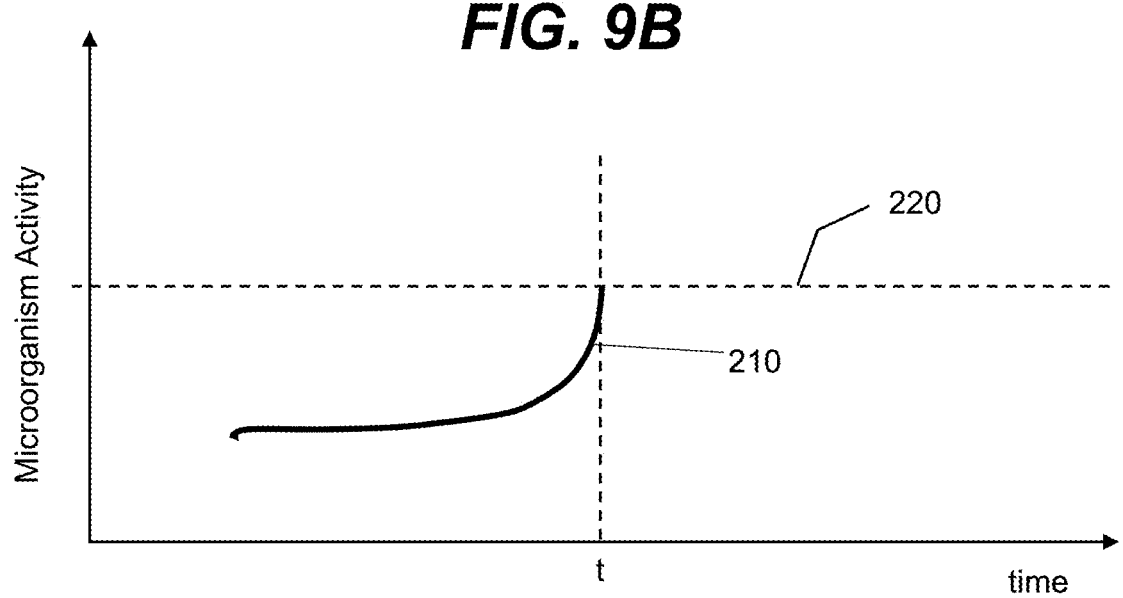

Turning now to FIGS. 9A and 9B, graphical representations that depict the operation of a scenario in which a first set of ultraviolet sources and a second set of ultraviolet sources are operated as a function of time. As shown in FIG. 9A, at section 200 of the graph, ultraviolet radiation from the second set of the radiation sources (e.g., blue-UV radiation) is used while determining whether there is any contamination of the toilet (e.g., based on an amplitude of a fluorescent signal sensed by a fluorescent sensor, visual data from a visual camera, and/or the like). For example, the toilet can be irradiated with an ultraviolet source that is capable of eliciting a fluorescent signal if microbial activity is present. The amplitude of the fluorescent signal can indicate the level of contamination and/or the amount of microbial activity. The toilet can be irradiated by blue-UV radiation over a prolonged period of time that ranges from tens of minutes to tens of hours while determining whether there is a fluorescent signal. During this time, the control system 111 (FIG. 10) and the fluorescent sensor component 154 (FIG. 10) operate in conjunction to monitor the amount of contamination present on the surface of the toilet.

In this example, FIG. 9B shows a sharp increase in the growth of microorganism activity as noted by reference element 210. When the level of microorganism activity approaches a predetermined contamination threshold 220 at time t that is indicative of a need for more intense ultraviolet irradiation treatment due to rapid growth of microbial activity, then the control system 111 will direct the first set of ultraviolet radiation sources (e.g., UV-C radiation) to perform the more intense ultraviolet irradiation treatment at the short burst of intensity that lasts at most a few minutes (FIG. 9A, reference number 230) starting at or shortly after time t. In an embodiment, the UV-C radiation is at most ten minutes long. In this manner, ultraviolet radiation (e.g., UV-C radiation) applied from the first set of ultraviolet radiation sources can bring microbial activity within appropriate limits by rapidly suppressing microbial activity on the surface of the object. The blue-UV radiation from the second set of radiation sources is used to maintain microbial activity within limits over an extended period of time, while the UV-C radiation from the first set of radiation sources is designed to rapidly suppress microbial activity. In an embodiment, the time operation for the blue-UV radiation is at least 100% longer than the time operation of the UV-C radiation.

In an embodiment, one or more surfaces of the toilet can include a photocatalyst. In an embodiment, the photocatalyst can be irradiated by an ultraviolet wavelength in the presence of water vapor to result in formation of hydroxyl group radicals and ROS that can effectively interact and disrupt proliferation of microorganisms. In an embodiment, the ultraviolet wavelength can be in the range of 360-380 nm. In another embodiment, the ultraviolet wavelength can be adjusted to be optimal for ROS and hydroxyl group radicals formation for each type of photocatalyst present. In an embodiment, the photocatalyst can comprise metal oxides, such as titanium oxide ($TiO_2$), copper, silver, copper/silver particles, and/or the like. The photocatalyst surfaces can be positioned to be in proximity and irradiated by ultraviolet light, and in close proximity to the surface of the toilet seat to ensure that created ROS and hydroxyl radicals react mostly on the surface of the toilet seat with microorganisms. In an embodiment, the position of the photocatalyst is such that at least 10% of resulting ROS and hydroxyl radicals reach the surface of the toilet seat.

In an embodiment, the toilet can also include UV reflective and/or UV diffusive surfaces designed to further recycle ultraviolet radiation. In an embodiment, such surfaces can be combined with partially UV transparent surfaces designed for further reflection, recycling and light guiding UV radiation. In an embodiment, such surfaces can comprise UV partially transparent material, such as fluoropolymers, $Al_2O_3$, sapphire, $SiO_2$, $CaF_2$, $MgF_2$, and/or the like.

As discussed herein, embodiments can sterilize various surfaces of a toilet, another bathroom fixture, a floor, and/or the like, using ultraviolet radiation. It is understood that a target dose of ultraviolet radiation can vary based on the type of microorganism being targeted and/or a level of sterilization desired. For example, a target dose can be selected to result in a multiple of a log reduction of the targeted microorganism. Illustrative target doses of ultraviolet radiation include: 3-5 $mJ/cm^2$ for Ebola virus; 6-12 $mJ/cm^2$ for *E-coli*; and 38 $mJ/cm^2$ for *Clostridium difficile* bacteria. However, embodiments can include different doses, which can be selected based on a higher desired log reduction and/or a surface on which the contaminant is present. For example, in another embodiment, the dose is selected to provide a 6 log reduction of the corresponding contaminant. To this extent, embodiments can use higher doses, such as 5-20 $mJ/cm^2$ for the Ebola virus.

The radiation power utilized should be sufficient to deliver the target dose of ultraviolet radiation within a target amount of time. The target amount of time can vary based on the particular application (e.g., particular surface being treated, typical amount of time available for sterilization, and/or the like). In an embodiment, the dose of ultraviolet radiation is delivered over the entire area of a seat of a toilet in less than one minute. In another embodiment, the target amount of time is less than or equal to five seconds for a given region when the ultraviolet radiation is delivered using a handheld device. However, it is understood that higher times are possible. In an embodiment, the time for delivering a dose to a surface of a toilet seat is any duration up to ten minutes. To ensure the target area receives at least the target dose, the beam of ultraviolet radiation can have only a reasonable variation in intensity. In an embodiment, the beam of ultraviolet radiation has a variation in intensity of less than forty percent across a surface area being illuminated. In a more particular embodiment, the beam of ultraviolet radiation varies by less than twenty percent across the surface area being illuminated.

Figure 10:
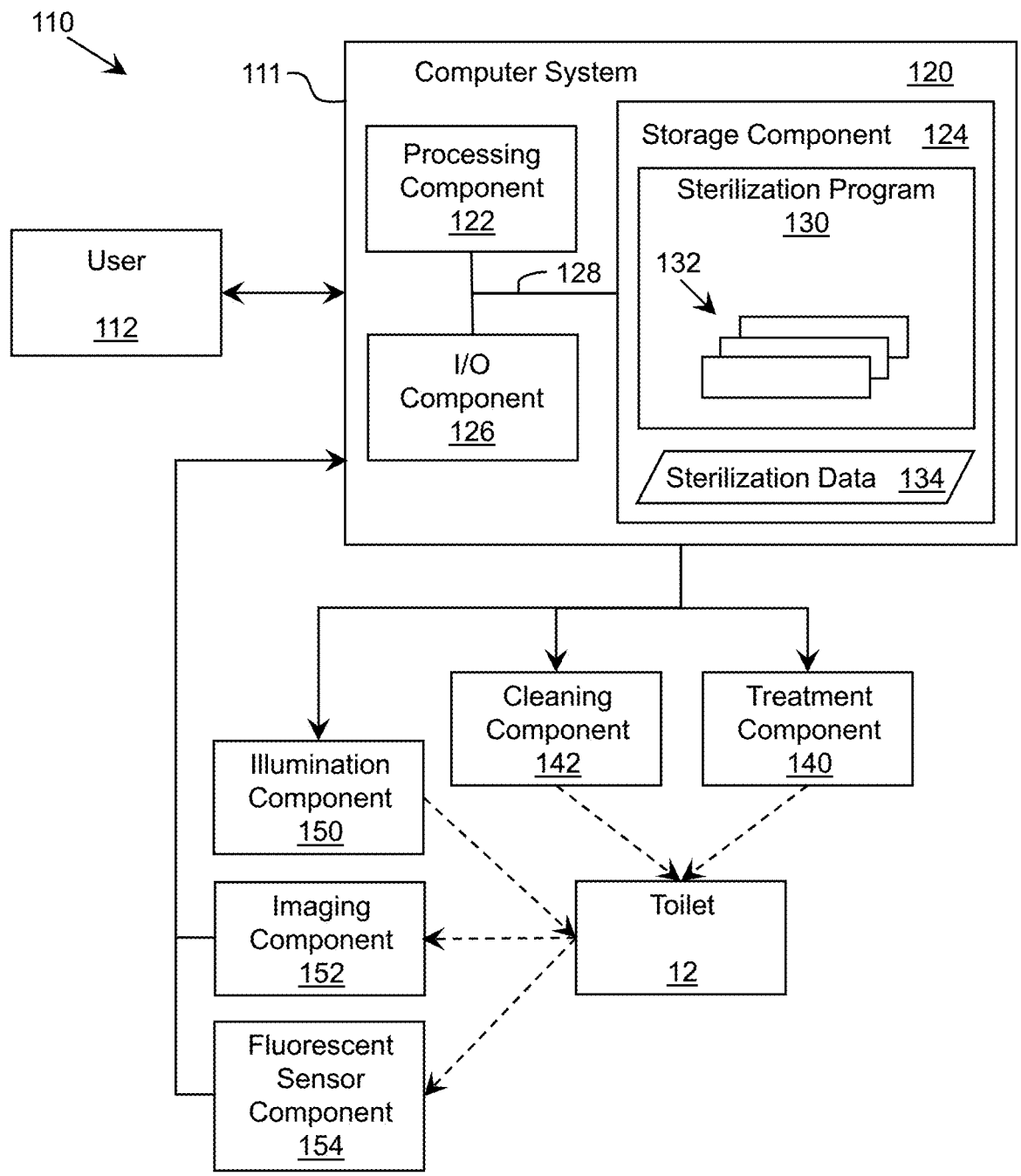
FIG. 10 shows an illustrative cleaning and sterilization system according to an embodiment.

In an embodiment, a control system manages operation of the various cleaning and/or sterilizing devices described herein according to a cleaning and sterilization process. To this extent, FIG. 10 shows an illustrative cleaning and sterilization system 110 according to an embodiment. In this case, the cleaning and sterilization system 110 includes a control system 111, which is configured to manage the operation of devices implemented as part of various components in order to clean and/or sterilize one or more surfaces of a toilet 12. However, it is understood that these are only illustrative of various components that can be implemented as part of a cleaning and sterilization system 110 described herein. Additionally, it is understood that a cleaning and sterilization system 110 described herein may not include one or more of the components shown and described in conjunction with FIG. 10 and/or can be utilized to clean and/or sterilize one or more different surfaces of a bathroom as described herein.

Regardless, the control system 111 is shown implemented as a computer system 120 that can perform a process described herein in order to clean and/or sterilize one or more surfaces of the toilet 12. In particular, the computer system 120 is shown including a sterilization program 130, which makes the computer system 120 operable to treat the surface(s) of the toilet 12 with ultraviolet radiation by performing a process described herein.

The computer system 120 is shown including a processing component 122 (e.g., one or more processors), a storage component 124 (e.g., a storage hierarchy), an input/output (I/O) component 126 (e.g., one or more I/O interfaces and/or devices), and a communications pathway 128. In general, the processing component 122 executes program code, such as the sterilization program 130, which is at least partially fixed in storage component 124. While executing program code, the processing component 122 can process data, which can result in reading and/or writing transformed data from/to the storage component 124 and/or the I/O component 126 for further processing. The pathway 128 provides a communications link between each of the components in the computer system 120. The I/O component 126 can comprise one or more human I/O devices, which enable a human user 112 to interact with the computer system 120 and/or one or more communications devices to enable a system user 112 to communicate with the computer system 120 using any type of communications link. To this extent, the sterilization program 130 can manage a set of interfaces (e.g., graphical user interface(s), application program interface, and/or the like) that enable human and/or system users 112 to interact with the sterilization program 130. Furthermore, the sterilization program 130 can manage (e.g., store, retrieve, create, manipulate, organize, present, etc.) the data, such as sterilization data 134, using any solution.

In any event, the computer system 120 can comprise one or more general purpose computing articles of manufacture (e.g., computing devices) capable of executing program code, such as the sterilization program 130, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the sterilization program 130 can be embodied as any combination of system software and/or application software.

Furthermore, the sterilization program 130 can be implemented using a set of modules 132. In this case, a module 132 can enable the computer system 120 to perform a set of tasks used by the sterilization program 130, and can be separately developed and/or implemented apart from other portions of the sterilization program 130. As used herein, the term "component" means any configuration of hardware, with or without software, which implements the functionality described in conjunction therewith using any solution, while the term "module" means program code that enables a computer system 120 to implement the actions described in conjunction therewith using any solution. When fixed in a storage component 124 of a computer system 120 that includes a processing component 122, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 120.

When the computer system 120 comprises multiple computing devices, each computing device can have only a portion of the sterilization program 130 fixed thereon (e.g., one or more modules 132). However, it is understood that the computer system 120 and the sterilization program 130 are only representative of various possible equivalent computer systems that may perform a process described herein. To this extent, in other embodiments, the functionality provided by the computer system 120 and the sterilization program 130 can be at least partially implemented by one or more computing devices that include any combination of general and/or specific purpose hardware with or without program code. In each embodiment, the hardware and program code, if included, can be created using standard engineering and programming techniques, respectively. In another embodiment, the control system 111 can be implemented without any computing device, e.g., using a closed loop circuit implementing a feedback control loop in which the outputs of one or more sensing devices are used as inputs to control the operation of one or more other devices. Illustrative aspects of the invention are further described in conjunction with the computer system 120. However, it is understood that the functionality described in conjunction therewith can be implemented by any type of control system 111.

Regardless, when the computer system 120 includes multiple computing devices, the computing devices can communicate over any type of communications link. Furthermore, while performing a process described herein, the computer system 120 can communicate with one or more other computer systems using any type of communications link. To this extent, while not shown for clarity, it is understood that the system user 112 can comprise a computer system configured as described in conjunction with the computer system 120. Regardless, the communications link can comprise any combination of various types of optical fiber, wired, and/or wireless links; comprise any combination of one or more types of networks; and/or utilize any combination of various types of transmission techniques and protocols.

As discussed herein, the sterilization program 130 enables the computer system 120 to treat surface(s) of the toilet 12. To this extent, the computer system 120 can operate one or more ultraviolet radiation sources included in the treatment component 140 to direct ultraviolet radiation onto one or more surfaces of the toilet 12 in order to sanitize the surface(s). Additionally, the computer system 120 can operate one or more devices (e.g., a wet brush, fluid source, air source, and/or the like) implemented as part of the cleaning component 142 to clean the surface(s) of debris and/or the like. Furthermore, the computer system 120 can receive feedback data regarding a surface of the toilet 12 from feedback device(s) included as part of an imaging component 152, fluorescent sensor component 154, and/or the like, of the toilet 12, each of which can include one or more sensing devices for acquiring data regarding the surface of the toilet 12 using any solution. For obtaining useful feedback data, the computer system 120 can operate one or more devices implemented in an illumination component 150 to illuminate some or all of the surfaces of the toilet 12 with ultraviolet radiation, visible light, and/or the like.

It is understood that the control system 111 can include other sensors to receive feedback data regarding the toilet 12 and the area surrounding the toilet. In an embodiment, the control system 111 can include environmental condition sensors such as a temperature sensor, a humidity sensor, a gas sensor, and/or the like. These sensors can be used by the computer system 120 in operating one or more devices implemented in the illumination component 150.

In an embodiment, the cleaning and sterilization system 110 includes control component(s), power component(s), control logic, and/or the like, capable of being implemented and operated in various different operating configurations, such as: contamination detection, during which a presence and/or location of a contaminant is determined; sterilization, during which identified contaminants are sterilized; and sterilization confirmation, during which the sterilization of contaminated areas is confirmed. Regardless, the control system 111 can operate and/or receive sterilization data 134 from various devices incorporated in the imaging component 152 and/or fluorescent sensor component 154, which can be processed in order to clean and/or sterilize the toilet 12 using a process described herein. To this extent, the control system 111 can be configured to distribute appropriate power and/or control signals to devices included in: a treatment component 140 (e.g., one or more ultraviolet light sources); a cleaning component 142 (e.g., one or more liquid sources, fans, air heating elements, brushes, and/or the like); an illumination component 150 (e.g., visible and/or ultraviolet light source(s)); an imaging component 152 (e.g., visible and/or ultraviolet camera(s), a reflectometer, and/or the like); and a fluorescent sensor component 154.

During a cleaning and/or sterilization process, the control system 111 can operate a set of ultraviolet source(s) in illumination component 150, which are configured to induce fluorescent signal(s) detected by fluorescent sensor(s) in the fluorescent sensor component 154. The fluorescent sensor component 154 can forward data regarding the detected fluorescent signal(s) and/or an evaluated presence of a contaminant (e.g., bacteria) for processing and use by the control system 111 during the cleaning and/or sterilization process. In an embodiment, the illumination component 150 includes visible light source(s) positioned and directed toward surface(s) of the toilet 12 similar to the ultraviolet source(s) of the illumination component 150. The control system 111 can operate the visible light source(s) in the illumination component 150 and/or imaging device(s) in the imaging component 152 to acquire image data for analysis by the control system 111. The control system 111 can store data regarding the image data (e.g., as sterilization data 134) and use the data derived from the image data to make adjustments to operation of the devices in the treatment component 140 and/or cleaning component 142 as part of the cleaning and/or sterilization process. To this extent, the control system 111 can adjust one or more aspects of a wash/dry schedule, a brushing schedule, an ultraviolet radiation schedule, and/or the like.

In an embodiment, the sterilization data 134 can also include the intensity, dosage, duration, wavelength, the type of radiation emitted from the first set of radiation sources and the second set of radiation sources, and the time duration of irradiation.

In an embodiment, the control system 111 can include a memory storage capable of recording the various data obtained from the feedback devices. To this extent, the control system 111 can receive the data for further analysis and optimization of the irradiation settings.

While described as being included in separate components 140, 150, it is understood that the ultraviolet source(s) used for sterilizing the surface(s) of the toilet 12 and the ultraviolet source(s) used to induce fluorescent signal(s) can be the same ultraviolet sources. For example, the control system 111 can adjust one or more aspects of operation of an ultraviolet source based on its use. To this extent, an ultraviolet source can be configured to be operated in an ultraviolet sterilizing mode, during which the ultraviolet source is operated at high power, and an ultraviolet fluorescent inducing mode, in which the ultraviolet source is operated at a lower power and/or different emission wavelength. The wavelength can be tuned, for example, using an ultraviolet source including an array of ultraviolet emitting devices having different wavelengths, and selecting the ultraviolet emitting device(s) within the array having the desired wavelength(s).

It is also understood that the ultraviolet radiation sources, whether included in separate components 140, 150, or the same component, can operate at different wavelengths. In an embodiment, the control system 111 can irradiate the seat surface of a toilet by a first set of ultraviolet sources and the second set of ultraviolet sources according to a plurality of predetermined optimal irradiation settings specified for various environmental conditions in which the toilet is located. In addition, the control system 111 can adjust the irradiation settings of the first set of ultraviolet sources and the second set of ultraviolet sources as a function of measurements obtained by the plurality of feedback devices described herein.

It is understood that the control system 111 can include one or more components for interfacing with a human user 112 (e.g., I/O component 126). To this extent, such components can include a set of inputs, which can enable the user 112 to affect the operation of one or more components of the cleaning and sterilization system 110. In an embodiment, the I/O component 126 can permit a user 112 to adjust at least one of the plurality of operating parameters for any of the components (e.g., cleaning component 142, treatment component 140, illumination component 150, imaging component 152, fluorescent sensor component 154, and/or the like). For example, a user 112 can make adjustments during the operation of different radiation sources and/or prior to initiating a treatment. In one embodiment, the I/O component 126 can include a set of buttons and/or a touch screen to enable the user 112 to specify various input selections regarding the operating parameters. Additionally, the interface can include an audio and/or visual presentation of the progress and/or results of the cleaning and/or sterilization process, e.g., via a screen, speakers, and/or the like. For example, the control system 111 can present data corresponding to an ultraviolet dose delivered during a current sterilization process, an amount of time remaining for a cleaning and/or sterilization process to complete, a current activity being performed as part of the cleaning and/or sterilization process, and/or the like. Furthermore, the control system 111 can provide data regarding a status of the toilet 12, a history of use and/or cleaning of the toilet 12, a history of any detected contaminants present on the toilet 12, and/or the like for presentation to a user 112, such as a building superintendent, or the like. In one embodiment, the I/O component 126 can allow a user 112 to interact with the control system 111 and to receive information regarding the toilet 12 and the treatment of the toilet 12. In an embodiment, the I/O component 126 can include a visual display for providing status information on the irradiation of the toilet 12 (e.g., time remaining, humidity, presence of water, or the like), status information of the surface, a simple visual indicator that displays whether irradiation is underway (e.g., an illuminated light), or if the irradiation is over (e.g., absence of an illuminated light). Furthermore, the control system 111 can operate one or more additional devices, which are implemented apart from cleaning and/or sterilization of the toilet 12. For example, a seat can include one or more heating elements, which the control system 111 can operate to heat the toilet seat for increased comfort for the user.

While shown and described herein as a method and system for cleaning and/or sterilizing a surface, such as a surface of a toilet, it is understood that aspects of the invention further provide various alternative embodiments. For example, in one embodiment, the invention provides a computer program fixed in at least one computer-readable medium, which when executed, enables a computer system to clean and/or treat a surface with ultraviolet light. To this extent, the computer-readable medium includes program code, such as the sterilization program 130, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the sterilization program 130, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for cleaning and/or sterilizing a surface with ultraviolet light. In this case, the generating can include configuring a computer system, such as the computer system 110, to implement a method of treating a surface with ultraviolet light described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    means for detecting radiation from a seat of a toilet;
    a first ultraviolet source configured to emit ultraviolet radiation at a first wavelength directed at the seat;
    a second ultraviolet source configured to emit ultraviolet radiation at a second wavelength directed at the seat; and
    a computer system for correlating the detected radiation with a presence of contamination on the seat and for operating at least one of: the first ultraviolet source or the second ultraviolet source, to sterilize the seat in response to the evaluating indicating the presence of contamination on the seat.

2. The system of claim 1, wherein the first ultraviolet source operates in a UV-C wavelength range.

3. The system of claim 1, wherein the second ultraviolet source emits ultraviolet radiation that excites a fluorescent signal from a target contaminant.

4. The system of claim 1, wherein the first ultraviolet source operates for at most ten minutes and operates in a UV-C wavelength range, and wherein the second ultraviolet source emits blue-ultraviolet light.

5. The system of claim 1, further comprising a set of fluid sources for cleaning the seat using a fluid.

6. The system of claim 5, further comprising a fan for circulating air over the seat after the cleaning.

7. The system of claim 1, wherein at least one of: the first ultraviolet source or the second ultraviolet source, emits ultraviolet radiation directed at a plurality of surfaces of the toilet.

8. The system of claim 1, wherein the means for detecting includes a fluorescent sensor for detecting a fluorescent signal.

9. The system of claim 1, wherein the means for detecting includes a visible light sensor for detecting visible light.

10. The system of claim 9, further comprising a visible light source, wherein the computer system further operates the visible light source and the visible light sensor to acquire feedback to determine an effectiveness of the sterilization.

11. A system comprising:
    a toilet including a seat;
    means for detecting radiation from the seat of the toilet;
    a first ultraviolet source configured to emit ultraviolet radiation at a first wavelength directed at the seat;
    a second ultraviolet source configured to emit ultraviolet radiation at a second wavelength directed at the seat, wherein at least one of: the first ultraviolet source or the second ultraviolet source, is isolated from an area for the seat by an ultraviolet transparent material; and a computer system for correlating the detected radiation with a presence of contamination on the seat and for operating at least one of: the first ultraviolet source or the second ultraviolet source, to sterilize the seat in response to the evaluating indicating the presence of contamination on the seat.

12. The system of claim 11, wherein the ultraviolet transparent material comprises fluoropolymer.

13. The system of claim 11, wherein the toilet further includes a cover for removably covering the seat, wherein at least one of: the first ultraviolet source or the second ultraviolet source, is located in the cover.

14. The system of claim 13, wherein the cover includes means for maintaining a target spacing between the cover and the seat.

15. The system of claim 11, wherein the first ultraviolet source operates in a UV-C wavelength range, and wherein the second ultraviolet source emits blue-ultraviolet light.

16. The system of claim 15, wherein the seat includes a photocatalyst.

17. A bathroom including:
a set of fixtures;
means for detecting radiation from a surface of at least one of the set of fixtures;
a first ultraviolet source configured to emit ultraviolet radiation at a first wavelength directed at the surface of the at least one of the set of fixtures;
a second ultraviolet source configured to emit ultraviolet radiation at a second wavelength directed at the surface of the at least one of the set of fixtures; and
a computer system for correlating the detected radiation with a presence of contamination on the surface of the at least one of the set of fixtures and for operating at least one of: the first ultraviolet source or the second ultraviolet source, to sterilize the surface of the at least one of the set of fixtures in response to the evaluating indicating the presence of contamination on the surface of the at least one of the set of fixtures.

18. The bathroom of claim 17, wherein the at least one of the set of fixtures includes one of: a toilet or a bidet.

19. The system of claim 17, wherein at least one of the first ultraviolet source or the second ultraviolet source, is mounted above the set of fixtures.

20. The system of claim 19, wherein the at least one of the first ultraviolet source or the second ultraviolet source mounted above the set of fixtures, emits a focused beam of ultraviolet radiation capable of being directed to a plurality of surfaces of at least one of the set of fixtures.

* * * * *